(12) United States Patent
Wehrman et al.

(10) Patent No.: US 8,569,057 B2
(45) Date of Patent: Oct. 29, 2013

(54) MONITORING PROTEIN TRAFFICKING USING BETA-GALACTOSIDASE REPORTER FRAGMENT COMPLEMENTATION

(75) Inventors: Thomas S. Wehrman, Mountain View, CA (US); Daniel Bassoni, Campbell, CA (US); William Raab, San Francisco, CA (US)

(73) Assignee: DiscoveRx Corporation, Fremont, CA (US)

( * ) Notice: Subject to any disclaimer, the term of this patent is extended or adjusted under 35 U.S.C. 154(b) by 0 days.

(21) Appl. No.: 13/531,230

(22) Filed: Jun. 22, 2012

(65) Prior Publication Data

US 2012/0329075 A1 Dec. 27, 2012

Related U.S. Application Data

(60) Provisional application No. 61/571,315, filed on Jun. 23, 2011.

(51) Int. Cl.
*C12N 5/02* (2006.01)

(52) U.S. Cl.
USPC .......................................................... 435/375

(58) Field of Classification Search
None
See application file for complete search history.

(56) References Cited

U.S. PATENT DOCUMENTS

| | | | |
|---|---|---|---|
| 4,378,428 A | 3/1983 | Farina et al. |
| 4,708,929 A | 11/1987 | Henderson |
| 5,037,735 A | 8/1991 | Khanna et al. |
| 5,106,950 A | 4/1992 | Farina et al. |
| 5,362,625 A | 11/1994 | Krevolin et al. |
| 5,464,747 A | 11/1995 | Eisenbeis et al. |
| 5,604,091 A | 2/1997 | Henderson |
| 5,643,734 A | 7/1997 | Henderson |
| 2003/0219848 A1 | 11/2003 | Naqvi et al. |
| 2007/0275397 A1 | 11/2007 | Wehrman et al. |
| 2009/0098588 A1 | 4/2009 | Wehrman et al. |
| 2010/0041052 A1 | 2/2010 | Feng et al. |
| 2010/0120063 A1 | 5/2010 | Bassoni et al. |
| 2010/0203555 A1 | 8/2010 | Wehrman et al. |
| 2010/0285451 A1 | 11/2010 | Blau et al. |
| 2011/0130543 A1 | 6/2011 | Stevens et al. |

FOREIGN PATENT DOCUMENTS

| | | | |
|---|---|---|---|
| WO | 92/03559 A2 | 3/1992 |
| WO | 96/19732 A1 | 6/1996 |
| WO | 00/39348 A1 | 7/2000 |
| WO | 01/00214 A1 | 1/2001 |
| WO | 01/60840 A2 | 8/2001 |

OTHER PUBLICATIONS

Emr, et al., "Invertase beta-galactosidase hybrid proteins fail to be transported from the endoplasmic reticulum in *Saccharomyces cerevisiae*", Mol. Cell. Biol. 1984, 4(11):2347-2355.
Drake, et al., "Trafficking of G protein-coupled receptors", Circ. Research, Sep. 15, 2006, vol. 99, No. 6, pp. 570-582.
International Search Report and Written Opinion, PCT/US12/043839, Sep. 7, 2012.
Jin, et al. "Disease-associated mutations affect GPR56 protein trafficking and cell surface expression", Human Molecular Genetics, 2007, vol. 16, No. 16, pp. 1972-1985.
Mollinari, et al., "Role of EDEM in the release of misfolded glycoproteins from the calnexin cycle", Science, vol. 299, Feb. 28, 2003, pp. 1397-1400.
Conn, et al., "G protein-coupled receptor trafficking in health and disease: lessons learned to prepare for therapeutic mutant rescue in vivo", Pharmacological Reviews, vol. 59, No. 3, 2007, pp. 225-250.
Stephenson, "Structure and trafficking of NMDA and GABA-a receptors", Biochemical Society Transactions (2006) vol. 34, part 5, pp. 877-881.
Petaja-Repo, et al., "Ligands act as pharmacological chaperones and increase the efficiency of delta opioid receptor maturation", The EMBO Journal, vol. 21, No. 7, 2002, pp. 1628-1637.
Lilley, et al. "A membrane protein required for dislocation of misfolded proteins from the ER", Nature, vol. 429, Jun. 24, 2004, pp. 834-840.
Li, et al., "Bone morphogenetic protein type II receptor mutations causing protein misfolding in heritable pulmonary arterial hypertension", Proceedings of the American Thoracic Society, vol. 7, 2010, pp. 395-398.
Zeng, et al., "Conserved extracellular cysteine pair in the M3 muscarinic acetylcholine receptor is essential for proper receptor cell surface localization but not for G protein coupling", Journal of Neurochemistry, 72, 1999, pp. 2404-2414.
Hammer, et al., "A novel enzyme complementation-based assay for monitoring G-protein-coupled receptor internalization", The FASEB Journal, vol. 21, Dec. 2007, pp. 3827-3834.
Dong, et al., "Regulation of G protein-coupled receptor export trafficking", Biochim Biophys Acta., Apr. 2007: 1768(4): 853-870.

*Primary Examiner* — Michael Pak
(74) *Attorney, Agent, or Firm* — David J. Aston; Peters Verny, LLP

(57) ABSTRACT

Methods and materials are disclosed for use in an enzyme fragment complementation assay using complementary fragments of β-galactosidase to study the trafficking of proteins in a cell. Compounds that bind to a target peptide have been found to affect protein folding and therefore trafficking. β-Galactosidase fragments, an enzyme donor (ED) and an enzyme acceptor (EA), are fused to a target peptide and to an intracellular compartment protein, wherein the compartment is involved in intracellular trafficking. Contacting the cell with a compound that binds to the target peptide results in enhanced movement of the protein through the cellular trafficking pathway comprised of the endoplasmic reticulum, Golgi apparatus, the plasma membrane, endosomes, etc. Using this approach, compounds that bind to a target peptide and alter its ability to traffic through the normal cellular pathway can be readily detected.

8 Claims, 6 Drawing Sheets

SEQUENCE LISTING

<160> NUMBER OF SEQ ID NOS: 8

<210> SEQ ID NO 1
<211> LENGTH: 24
<212> TYPE: PRT
<213> ORGANISM: homo sapiens

<400> SEQUENCE: 1

Arg Val Ile Ile Leu Met Val Trp Ile Val Ser Gly Leu Thr Ser Phe
1               5                   10                  15

Leu Pro Ile Gln Met His Trp Tyr
            20

<210> SEQ ID NO 2
<211> LENGTH: 52
<212> TYPE: PRT
<213> ORGANISM: artificial
<220> FEATURE:
<223> OTHER INFORMATION: synthetic peptide sequence (H31R)

<400> SEQUENCE: 2

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala Arg Pro
            20                  25                  30

Pro Phe Ala Ser Trp Arg Asn Ser Glu Glu Ala Arg Thr Asp Arg Pro
        35                  40                  45

Ser Gln Gln Leu
    50

<210> SEQ ID NO 3
<211> LENGTH: 52
<212> TYPE: PRT
<213> ORGANISM: artificial
<220> FEATURE:
<223> OTHER INFORMATION: synthetic peptide sequence (F34Y)

<400> SEQUENCE: 3

Met Gly Val Ile Thr Asp Ser Leu Ala Val Val Leu Gln Arg Arg Asp
1               5                   10                  15

Trp Glu Asn Pro Gly Val Thr Gln Leu Asn Arg Cys Ala Ala His Pro
            20                  25                  30

Pro Tyr Ala Ser Trp Arg Asn Ser Glu Glu Ala Arg Thr Asp Arg Pro
        35                  40                  45

Ser Gln Gln Leu
    50

<210> SEQ ID NO 4
<211> LENGTH: 52
<212> TYPE: PRT
<213> ORGANISM: artificial
<220> FEATURE:
<223> OTHER INFORMATION: synthetic peptide sequence (E41Q)

<400> SEQUENCE: 4

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

```
Pro Phe Ala Ser Trp Arg Asn Ser Gln Glu Ala Arg Thr Asp Arg Pro
         35                  40                  45

Ser Gln Gln Leu
    50

<210> SEQ ID NO 5
<211> LENGTH: 52
<212> TYPE: PRT
<213> ORGANISM: artificial
<220> FEATURE:
<223> OTHER INFORMATION: synthetic peptide sequence (N39D)

<400> SEQUENCE: 5

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asp Ser Glu Glu Ala Arg Thr Asp Arg Pro
         35                  40                  45

Ser Gln Gln Leu
    50

<210> SEQ ID NO 6
<211> LENGTH: 43
<212> TYPE: PRT
<213> ORGANISM: artificial
<220> FEATURE:
<223> OTHER INFORMATION: synthetic peptide sequence (Truncated)

<400> SEQUENCE: 6

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asp Ser Glu Glu Ala
         35                  40

<210> SEQ ID NO 7
<211> LENGTH: 42
<212> TYPE: PRT
<213> ORGANISM: artificial
<220> FEATURE:
<223> OTHER INFORMATION: synthetic peptide sequence (ProLink (TM))

<400> SEQUENCE: 7

Asp Ser Leu Ala Val Val Leu Gln Arg Arg Asp Trp Glu Asn Pro Gly
1               5                   10                  15

Val Thr Gln Leu Asn Arg Leu Ala Ala Arg Pro Pro Phe Ala Ser Trp
            20                  25                  30

Arg Asn Ser Glu Glu Ala Arg Thr Asp Arg
         35                  40

<210> SEQ ID NO 8
<211> LENGTH: 991
<212> TYPE: PRT
<213> ORGANISM: artificial
<220> FEATURE:
<223> OTHER INFORMATION: synthetic peptide sequence

<400> SEQUENCE: 8

Met Gly Val Ile Thr Asp Ser Leu Ala Val Val Ala Arg Thr Asp Arg
1               5                   10                  15
```

-continued

```
Pro Ser Gln Gln Leu Arg Ser Leu Asn Gly Glu Trp Arg Phe Ala Trp
         20                  25                  30

Phe Pro Ala Pro Glu Ala Val Pro Glu Ser Trp Leu Glu Cys Asp Leu
         35                  40                  45

Pro Glu Ala Asp Thr Val Val Pro Ser Asn Trp Gln Met His Gly
 50                  55                  60

Tyr Asp Ala Pro Ile Tyr Thr Asn Val Thr Tyr Pro Ile Thr Val Asn
 65                  70                  75                  80

Pro Pro Phe Val Pro Thr Glu Asn Pro Thr Gly Cys Tyr Ser Leu Thr
                 85                  90                  95

Phe Asn Val Asp Glu Ser Trp Leu Gln Glu Gly Gln Thr Arg Ile Ile
                100                 105                 110

Phe Asp Gly Val Asn Ser Ala Phe His Leu Trp Cys Asn Gly Arg Trp
                115                 120                 125

Val Gly Tyr Gly Gln Asp Ser Arg Leu Pro Ser Glu Phe Asp Leu Ser
         130                 135                 140

Ala Phe Leu Arg Ala Gly Glu Asn Arg Leu Ala Val Met Val Leu Arg
145                 150                 155                 160

Trp Ser Asp Gly Ser Tyr Leu Glu Asp Gln Asp Met Trp Arg Met Ser
                165                 170                 175

Gly Ile Phe Arg Asp Val Ser Leu Leu His Lys Pro Thr Thr Gln Ile
                180                 185                 190

Ser Asp Phe His Val Ala Thr Arg Phe Asn Asp Asp Phe Ser Arg Ala
         195                 200                 205

Val Leu Glu Ala Glu Val Gln Met Cys Gly Glu Leu Arg Asp Tyr Leu
 210                 215                 220

Arg Val Thr Val Ser Leu Trp Gln Gly Glu Thr Gln Val Ala Ser Gly
225                 230                 235                 240

Thr Ala Pro Phe Gly Gly Glu Ile Ile Asp Glu Arg Gly Gly Tyr Ala
                245                 250                 255

Asp Arg Val Thr Leu Arg Leu Asn Val Glu Asn Pro Lys Leu Trp Ser
             260                 265                 270

Ala Glu Ile Pro Asn Leu Tyr Arg Ala Val Val Glu Leu His Thr Ala
         275                 280                 285

Asp Gly Thr Leu Ile Glu Ala Glu Cys Asp Val Gly Phe Arg Glu Val
 290                 295                 300

Arg Ile Glu Asn Gly Leu Leu Leu Leu Asn Gly Lys Pro Leu Leu Ile
305                 310                 315                 320

Arg Gly Val Asn Arg His Glu His His Pro Leu His Gly Gln Val Met
                325                 330                 335

Asp Glu Gln Thr Met Val Gln Asp Ile Leu Leu Met Lys Gln Asn Asn
             340                 345                 350

Phe Asn Ala Val Arg Cys Ser His Tyr Pro Asn His Pro Leu Trp Tyr
         355                 360                 365

Thr Leu Cys Asp Arg Tyr Gly Leu Tyr Val Val Asp Glu Ala Asn Ile
 370                 375                 380

Glu Thr His Gly Met Val Pro Met Asn Arg Leu Thr Asp Asp Pro Arg
385                 390                 395                 400

Trp Leu Pro Ala Met Ser Glu Arg Val Thr Arg Met Val Gln Arg Asp
                405                 410                 415

Arg Asn His Pro Ser Val Ile Ile Trp Ser Leu Gly Asn Glu Ser Gly
             420                 425                 430

His Gly Ala Asn His Asp Ala Leu Tyr Arg Trp Ile Lys Ser Val Asp
         435                 440                 445
```

-continued

Pro Ser Arg Pro Val Gln Tyr Glu Gly Gly Ala Asp Thr Thr Ala
    450                 455             460

Thr Asp Ile Ile Cys Pro Met Tyr Ala Arg Val Asp Glu Asp Gln Pro
465             470                 475             480

Phe Pro Ala Val Pro Lys Trp Ser Ile Lys Lys Trp Leu Ser Leu Pro
                485                 490                 495

Gly Glu Thr Arg Pro Leu Ile Leu Cys Glu Tyr Ala His Ala Met Gly
            500                 505             510

Asn Ser Leu Gly Gly Phe Ala Lys Tyr Trp Gln Ala Phe Arg Gln Tyr
        515                 520             525

Pro Arg Leu Gln Gly Gly Phe Val Trp Asp Trp Val Asp Gln Ser Leu
        530                 535             540

Ile Lys Tyr Asp Glu Asn Asn Pro Trp Ser Ala Tyr Gly Gly Asp Phe
545                 550                 555             560

Gly Asp Thr Pro Asn Asp Arg Gln Phe Cys Met Asn Gly Leu Val Phe
                565                 570             575

Ala Asp Arg Thr Pro His Pro Ala Leu Thr Glu Ala Lys His Gln Gln
            580                 585             590

Gln Phe Phe Gln Phe Arg Leu Ser Gly Gln Thr Ile Glu Val Thr Ser
        595                 600             605

Glu Tyr Leu Phe Arg His Ser Asp Asn Glu Leu Leu His Trp Met Val
        610                 615             620

Ala Leu Asp Gly Lys Pro Leu Ala Ser Gly Glu Val Pro Leu Asp Val
625                 630                 635             640

Ala Pro Gln Gly Lys Gln Leu Ile Glu Leu Pro Glu Leu Pro Gln Pro
                645                 650             655

Glu Ser Ala Gly Gln Leu Trp Leu Thr Val Arg Val Val Gln Pro Asn
            660                 665             670

Ala Thr Ala Trp Ser Glu Ala Gly His Ile Ser Ala Trp Gln Gln Trp
        675                 680             685

Arg Leu Ala Glu Asn Leu Ser Val Thr Leu Pro Ala Ala Ser His Ala
        690                 695             700

Ile Pro His Leu Thr Thr Ser Glu Met Asp Phe Cys Ile Glu Leu Gly
705                 710                 715             720

Asn Lys Arg Trp Gln Phe Asn Arg Gln Ser Gly Phe Leu Ser Gln Met
                725                 730             735

Trp Ile Gly Asp Lys Lys Gln Leu Leu Thr Pro Leu Arg Asp Gln Phe
            740                 745             750

Thr Arg Ala Pro Leu Asp Asn Asp Ile Gly Val Ser Glu Ala Thr Arg
        755                 760             765

Ile Asp Pro Asn Ala Trp Val Glu Arg Trp Lys Ala Ala Gly His Tyr
        770                 775             780

Gln Ala Glu Ala Ala Leu Leu Gln Cys Thr Ala Asp Thr Leu Ala Asp
785                 790                 795             800

Ala Val Leu Ile Thr Thr Ala His Ala Trp Gln His Gln Gly Lys Thr
                805                 810             815

Leu Phe Ile Ser Arg Lys Thr Tyr Arg Ile Asp Gly Ser Gly Gln Met
            820                 825             830

Ala Ile Thr Val Asp Val Glu Val Ala Ser Asp Thr Pro His Pro Ala
        835                 840             845

Arg Ile Gly Leu Asn Cys Gln Leu Ala Gln Val Ala Glu Arg Val Asn
        850                 855             860

Trp Leu Gly Leu Gly Pro Gln Glu Asn Tyr Pro Asp Arg Leu Thr Ala

-continued

| | | | | | | | | | | | | |
|---|---|---|---|---|---|---|---|---|---|---|---|---|
|865| | | | |870| | | | |875| | |880|
|Ala|Cys|Phe|Asp|Arg|Trp|Asp|Leu|Pro|Leu|Ser|Asp|Met|Tyr|Thr|Pro|
| | | | |885| | | | |890| | | | |895| |
|Tyr|Val|Phe|Pro|Ser|Glu|Asn|Gly|Leu|Arg|Cys|Gly|Thr|Arg|Glu|Leu|
| | | |900| | | | |905| | | | |910| | |
|Asn|Tyr|Gly|Pro|His|Gln|Trp|Arg|Gly|Asp|Phe|Gln|Phe|Asn|Ile|Ser|
| | |915| | | | |920| | | | |925| | | |
|Arg|Tyr|Ser|Gln|Gln|Gln|Leu|Met|Glu|Thr|Ser|His|Arg|His|Leu|Leu|
| |930| | | | |935| | | | |940| | | | |
|His|Ala|Glu|Glu|Gly|Thr|Trp|Leu|Asn|Ile|Asp|Gly|Phe|His|Met|Gly|
|945| | | | |950| | | | |955| | | | |960|
|Ile|Gly|Gly|Asp|Asp|Ser|Trp|Ser|Pro|Ser|Val|Ser|Ala|Glu|Phe|Gln|
| | | |965| | | | |970| | | | |975| | |
|Leu|Ser|Ala|Gly|Arg|Tyr|His|Tyr|Gln|Leu|Val|Trp|Cys|Gln|Lys| |
| | | |980| | | | |985| | | | |990| | |

MONITORING PROTEIN TRAFFICKING USING BETA-GALACTOSIDASE REPORTER FRAGMENT COMPLEMENTATION

CROSS-REFERENCE TO RELATED APPLICATIONS

This application claims priority from U.S. Provisional Patent Application No. 61/571,315 filed on Jun. 23, 2011, which is hereby incorporated by reference.

STATEMENT OF GOVERNMENTAL SUPPORT

None.

REFERENCE TO SEQUENCE LISTING, COMPUTER PROGRAM, OR COMPACT DISK

The instant application contains a Sequence Listing which has been submitted as an ASCII text file and is hereby incorporated by reference in its entirety. This text file was created on Jun. 21, 2012, is named "3817_36_1_Seq_List.txt" and is 12,412 bytes in size.

BACKGROUND OF THE INVENTION

1. Field of the Invention

The present invention relates to the field of assays for measuring the intracellular movement ("trafficking") of proteins containing at least one transmembrane domain, such as a cell surface receptor.

2. Related Art

Presented below is background information on certain aspects of the present invention as they may relate to technical features referred to in the detailed description, but not necessarily described in detail. That is, individual parts or methods used in the present invention may be described in greater detail in the materials discussed below, which materials may provide further guidance to those skilled in the art for making or using certain aspects of the present invention as claimed. The discussion below should not be construed as an admission as to the relevance of the information to any claims herein or the prior art effect of the material described.

Protein synthesis and its processing are highly regulated events done in a tightly scrutinized and controlled manner at the transcriptional, translational and post-translational levels involving the endoplasmic reticulum (ER), Golgi apparatus, the plasma membrane, endosome, phagosome and lysosome. Protein synthesis and its folding occur in endoplasmic reticulum. The proteins adopt distinct conformations and mature before reaching their site of action. The process involves strict quality control mechanisms that ensure that improperly/misfolded proteins are accumulated in the ER and are later degraded via the proteosome pathway. In this manner, only the preciously folded proteins are allowed to exit ER and follow the maturation pathway before reaching their site of action.

Trans-membrane proteins such as GPCR's are a part of large family of cell-surface receptors and central to present day drug discovery research. All GPCR's share some unique features of having an extracellular N-terminal fragment, seven trans-membrane domains forming a trans-membrane core, three exoloops, three cytoloops and an intracellular C-terminal segment. However, the different sections vary in size, an indication of their diverse structures and functions. (Attwood T K, Findlay J B, 1994, Fingerprinting G-protein coupled receptors, *Protein Eng.* 7 (2): 195-203; Kolakowski L F Jr, 1994 GCRDb: a G-protein-coupled receptor database, *Receptors Channels* 2 (1): 1-7; Foord S M, Bonner T I, Neubig R R, Rosser E M, Pin J P, Davenport A P, Spedding M, Harmar A J, 2005, International Union of Pharmacology. XLVI. G protein-coupled receptor list, *Pharmacol Rev* 57 (2): 279-88, *InterPro*). GPCR's broadly can be grouped into six classes based on sequence homology and functional similarity, as follows.

| | |
|---|---|
| Class A | (Rhodopsin-like) |
| Class B | (Secretin receptor family) |
| Class C | (Metabotropic glutamate/pheromone) |
| Class D | (Fungal mating pheromone receptors) |
| Class E | (Cyclic AMP receptors) |
| Class F | (Frizzled/Smoothened) |

A GPCR adopts a tertiary structure with the seven transmembrane helices which forms a cavity within the plasma membrane and the cavity serves as a ligand-binding domain. Another common structural feature amongst GPCR's is palmitoylation of one or more sites of the C-terminal tail or the intracellular loops which has the effect of targeting the receptor to cholesterol and sphingolipid-rich microdomains of the plasma membrane called lipid rafts and have a role to participate in rapid receptor signaling.

Ion channels represent another class of membrane protein complexes that play an important function of facilitating the diffusion of ions across the biological membranes. They act as electrical insulators and provide a high conducting, hydrophilic pathway across the hydrophobic interior of the membrane. Their mode of action is highly gated and they switch their confirmations between closed and open states. Depending on the chemical and physical modulators that control the gating activity-ion channels can be classified into the following groups:

1. Ligand-gated channels
2. Voltage-gated channels
3. Second-messenger gated channels
4. Mechanosensitive channels
5. Gap junctions There are a number of human disorders that can result from misfolded/mutated protein ion channels. For example: Inherited long QT syndrome (LQT), which can cause failure of normal inactivation to increase late $Na^+$ current and prolong the action potential. A number of LQT2-linked mutations have been identified in hERG channels. A common mechanism that has emerged and been linked to LQT2 diseases involves protein trafficking defects which reduce the delivery of channels to the cell membrane. After synthesis and core-glycosylations in ER, hERG protein is exported to the Golgi apparatus for complex glycosylation, sorting and eventual insertion into the surface membrane. Once in Golgi apparatus, hERG channels undergo complex glycosylation. A number of biological functions have been suggestive to be a result of core- and complex glycosylation, including promoting proper protein folding, ER export and regulating protein stability.

Therefore, monitoring the activation and/or inhibition of the trafficking can lead to dramatic cellular effects and will help in elucidating the role of trans-membrane proteins in their normal physiological functionality. To develop the therapies and drugs potentially useful in regulating trafficking in healthy and disease states and to understand fate of a protein through the trafficking pathway depends on monitoring the progression of the protein at different stages in cell.

Specific Patents and Publications

US Patent Application 2010/0041052, "Receptor tyrosine kinase assays," published Feb. 18, 2010, owned by the present assignee, discloses methods for detecting phosphorylation of receptor tyrosine kinases upon activation which employ weakly complementing fragments of beta-galactosidase.

US Patent Application 2010/0203555, "Wild-type receptor assays," published Aug. 12, 2010, owned by the present assignee, discloses methods for determining ligand activation of receptors using fusion proteins comprising beta-galactosidase fragments.

US Patent Application 2010/0120063, "GPCR arrestin assays," published May 13, 2010, owned by the present assignee, discloses assays for candidate compounds affecting GPCR activity employing fusion proteins comprising beta-galactosidase fragments in which one of the fragments is fused to arrestin.

Hammer et al., "A novel enzyme complementation-based assay for monitoring G-protein-coupled receptor internalization," FASEB Journal, December, 2007, vol. 21, pp 3827-3834, discloses monitoring the internalization of GPCRs to the endosome using beta-galactosidase complementation assays.

Jin et al., "Disease-associated mutations affect GPR56 protein trafficking and cell surface expression," Human Molecular Genetics, 2007, Vol. 16, No. 16, pp 1972-1985, discloses the effect of mutant and wild-type G protein-coupled receptor (GPR) 56 on protein trafficking. GPR56 mutants produce proteins that have deficient trafficking properties to the plasma membrane or for secretion, thus causing the proteins to remain in the endoplasmic reticulum and/or Golgi.

As described in Lilley and Ploegh, "A membrane protein required for dislocation of misfolded proteins from the ER," Nature 429:834-840 (2004), after insertion into the endoplasmic reticulum (ER), proteins that fail to fold there are destroyed. Through a process termed dislocation, such misfolded proteins arrive in the cytosol, where ubiquitination, deglycosylation and finally proteasomal proteolysis dispense with the unwanted polypeptides. Most misfolded secretory proteins remain in the endoplasmic reticulum (ER) and are degraded by ER-associated degradation (ERAD).

BRIEF SUMMARY OF THE INVENTION

The following brief summary is not intended to include all features and aspects of the present invention, nor does it imply that the invention must include all features and aspects discussed in this summary.

The present invention comprises methods and compositions for monitoring the progression of the target peptide through the trafficking pathway. One aspect of the invention includes the use of a reduced affinity enzyme complementation reporter system. In certain embodiments, the reduced affinity enzyme complementation reporter system is a reduced affinity β-galactosidase complementation reporter system. Also provided are systems and kits for use in practicing embodiments of the methods.

In certain embodiments, the present invention comprises a method of detecting the effect of a test compound on trafficking of a target peptide to a subcellular compartment, comprising the steps of providing a cell expressing therein (a) first fusion protein comprising a peptide localized to said subcellular compartment and a first β-galactosidase fragment; and (b) a second fusion protein comprising a target peptide having a sequence making it subject to altered protein trafficking and a second β-galactosidase fragment; wherein said first and second β-galactosidase fragments have an affinity for each other such that an active β-galactosidase enzyme is produced only when the first and second β-galactosidase fragments are in the same subcellular compartment; and adding to said cell the test compound, wherein binding of the test compound to the target peptide changes protein trafficking and results in a change in β-galactosidase activity.

In certain embodiments, the present invention comprises a method wherein said target peptide is a cell membrane protein. In certain embodiments, the present invention comprises a method wherein said cell membrane protein is selected from the group consisting of a G protein coupled receptor ("GPCR") and an ion channel. In certain embodiments, the present invention comprises a method wherein the sequence making it subject to altered protein trafficking comprises a single amino acid mutation. In certain embodiments, the present invention comprises a method wherein said first β-galactosidase fragment is a variant enzyme donor fragment. In certain embodiments, the present invention comprises a method wherein said second β-galactosidase fragment is localized to an endosome.

In certain embodiments, the present invention comprises a method of determining an effect of a compound on trafficking of a target peptide, comprising: providing a cell having an endoplasmic reticulum ("ER"), said cell comprising therein a first fusion protein comprising the target peptide fused to a first β-galactosidase fragment; and a second fusion protein comprising a protein localized to sub-cellular compartment fused to a second β-galactosidase fragment; wherein said subcellular compartment is selected from the group consisting of i. cytosol; ii. Golgi apparatus; iii. plasma membrane; and iv. endosome; said first and second β-galactosidase fragments have an affinity for each other to complement and produce an active β-galactosidase enzyme when the first and second β-galactosidase units are in close proximity; adding to said cell a compound that affects release of the target peptide from the ER; and evaluating said cell for active β-galactosidase activity to determine whether the first and second fusion protein interact in said sub-cellular compartment as a result of release of the target peptide from the ER being affected by the compound.

In certain embodiments, the present invention comprises a method wherein said cell is a mammalian cell. In certain embodiments, the present invention comprises a method wherein said target peptide is a cell membrane protein. In certain embodiments, the present invention comprises a method wherein said cell membrane protein is a G-protein coupled receptor ("GPCR"). In certain embodiments, the present invention comprises a method wherein the GPCR is one of a beta adrenergic receptor, histamine receptor, serotonin receptor, dopamine receptor, muscarinic receptor and angiotensin receptor wherein said first β-galactosidase fragment is an enzyme donor fragment. In certain embodiments, the present invention comprises a method wherein said subcellular compartment is an endosome. In certain embodiments, the present invention comprises a wherein said second β-galactosidase fragment is localized to an endosome by a FYVE domain in said second fusion protein.

In certain embodiments, the present invention comprises a kit for carrying out monitoring protein trafficking of a target peptide, said target peptide being substantially retained in the ER without having contact with a compound, comprising genetic constructs for transforming a eukaryotic cell, said genetic constructs in one or more expression vectors, comprising genetic constructs encoding (a) first fusion protein comprising a peptide localized to a subcellular compartment and a first β-galactosidase fragment; and (b) a second fusion protein comprising a peptide having a sequence making it subject to altered protein trafficking and a second β-galactosidase fragment. In certain embodiments, the present invention comprises a kit wherein said target peptide is a GPCR modified to be ER-bound due to a misfolding mutation in the GPCR. In certain embodiments, the present invention comprises a kit wherein said GPCR is selected from the group consisting of beta adrenergic receptor, histamine receptor, serotonin receptor, dopamine receptor, muscarinic receptor and angiotensin receptor.

In certain embodiments, the peptide in the second fusion protein is a peptide that constitutes all or a portion of a cell membrane protein. The cell membrane protein may be a G protein coupled receptor ("GPCR").

For the enzyme fragments, the first β-galactosidase fragment is preferably an enzyme donor fragment. The second β-galactosidase fragment then is an enzyme acceptor fragment and may be localized to an endosome.

Aspects of the present invention include determining an effect of a compound on trafficking of a target peptide, comprising:
(1) providing a cell having an endoplasmic reticulum ("ER"), said cell comprising therein a first fusion protein comprising the target peptide fused to a first β-galactosidase fragment and a second fusion protein comprising a protein localized to sub-cellular compartment fused to a second β-galactosidase fragment wherein said subcellular compartment is selected from the group consisting of
  a. cytosol;
  b. Golgi apparatus;
  c. plasma membrane; and
  d. endosome;
where said first and second β-galactosidase fragments have an affinity for each other to complement and produce an active β-galactosidase enzyme when the first and second β-galactosidase units are in close proximity, (2) adding to said cell a compound that affects release of the target peptide from the ER, and (3) evaluating said cell for active β-galactosidase activity to determine whether the first and second fusion protein interact in said sub-cellular compartment as a result of release of the target peptide from the ER being affected by the compound.

The cell containing the present fusion constructs may be a mammalian cell, and it may be grown in isolation in a culture for use in the present assays.

The target peptide may be a cell membrane protein. In certain embodiments, the cell membrane protein is a G-protein coupled receptor ("GPCR") where the GPCR is selected from the group consisting of: beta adrenergic receptor, histamine receptor, serotonin receptor, dopamine receptor, muscarinic receptor and angiotensin receptor. In certain embodiments, the GPCR contains a mutation causing misfolding of the GPCR and retention in the ER.

In certain embodiments, the first β-galactosidase fragment is an enzyme donor fragment. The subcellular compartment is an endosome. The second β-galactosidase fragment is localized to an endosome by a FYVE domain in said second fusion protein.

In certain embodiments, nucleic acids encoding the first and second fusion proteins are expressed in the cell, where the nucleic acids may be introduced into the cell sequentially or simultaneously. In certain embodiments, the method further includes contacting the cell with a compound prior to the evaluating step. The compound may be tested for binding to the target peptide.

In certain embodiments, the first β-galactosidase fragment has a binding affinity for the second β-galactosidase fragment that is lower than a β-galactosidase fragment consisting of amino acids 3 to 92 of E. coli wild-type β-galactosidase. In certain embodiments, the first β-galactosidase fragment comprises at least one amino acid variation as compared to β-galactosidase fragment consisting on amino acids 3 to 92 of E. coli wild-type β-galactosidase. In certain embodiments, the at least one amino acid variation is a substitution or a deletion. In certain embodiments, the variation occurs between residues 31 and 41. In certain embodiments, the cell is a mammalian cell.

Also provided are kits for monitoring protein trafficking of a target peptide, said target peptide being substantially retained in the ER without having contact with a compound, comprising genetic constructs for transforming a eukaryotic cell, said genetic constructs in one or more expression vectors, comprising genetic constructs encoding: (1) a first fusion protein comprising a target peptide retained in the ER and a first β-galactosidase fragment and (2) a second fusion protein comprising a protein localized to sub-cellular compartment and a second β-galactosidase fragment.

In certain embodiments, one of the β-galactosidase fragments is a variant minimal N-terminal β-galactosidase peptide.

In certain embodiments, the target peptide is a GPCR modified to be ER-bound. The GPCR may be selected from the group consisting of beta adrenergic receptor, histamine receptor, serotonin receptor, dopamine receptor, muscarinic receptor and angiotensin receptor.

Also provided are kits comprising: (a) a first nucleic acid encoding a fusion protein comprising a first β-galactosidase fragment and a target peptide; and (b) a second nucleic acid encoding a fusion protein that comprises a sub-cellular compartment localized protein and a second β-galactosidase fragment; wherein the first and second β-galactosidase fragments have a reduced affinity for each other as compared to wild type β-galactosidase fragments. In certain embodiments the first β-galactosidase fragment is a variant minimal N-terminal β-galactosidase peptide and has a binding affinity for said second β-galactosidase fragment that is lower than a β-galactosidase fragment consisting of amino acids 3 to 92 of E. coli wild-type β-galactosidase. In certain embodiments, the first vector comprises a restriction site positioned on a vector such that when a protein coding sequence is inserted into the vector using the restriction site, the vector encodes a fusion protein of the protein and the β-galactosidase fragment. In certain embodiments, the kit further comprises a mammalian cell. In certain embodiments the kit further comprises a β-galactosidase substrate.

DETAILED DESCRIPTION OF THE PREFERRED EMBODIMENT

Definitions

Figure 1:
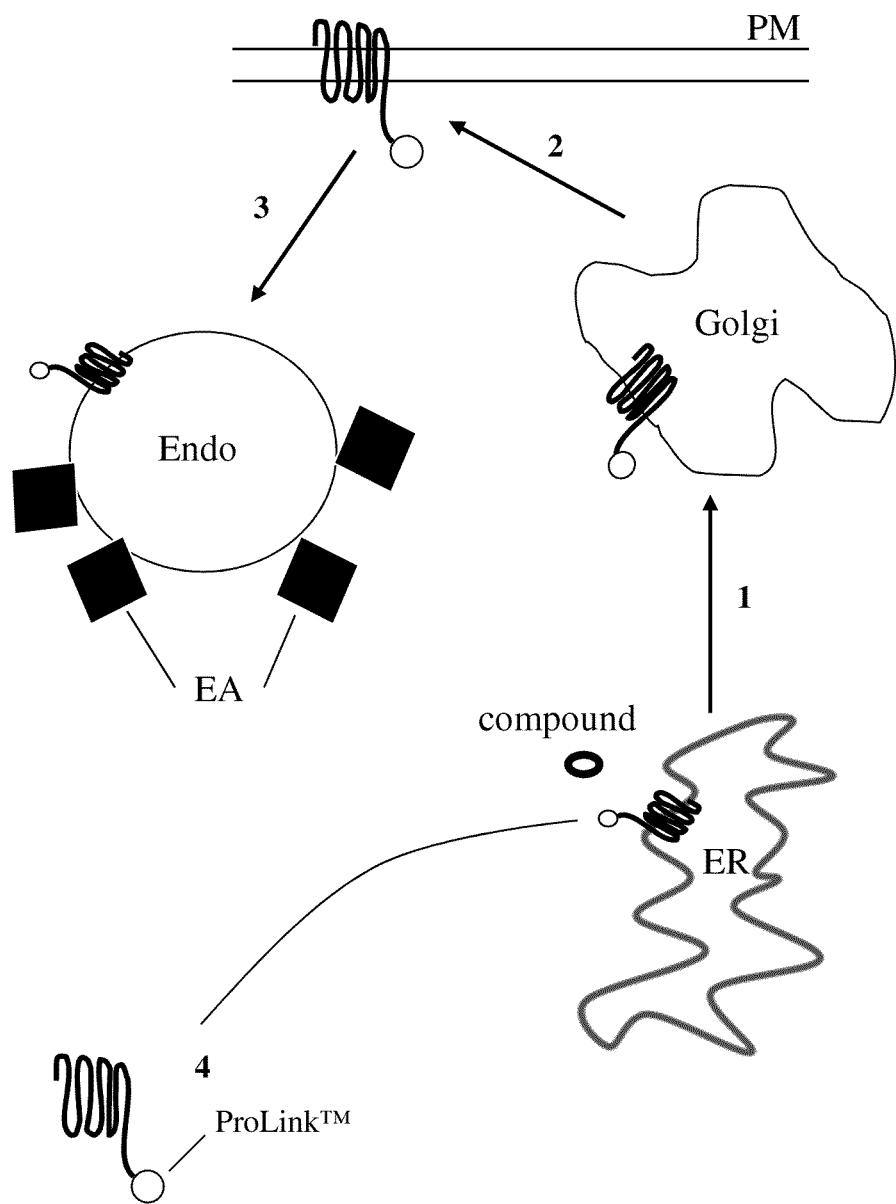
FIG. 1 is a diagrammatic representation of a biosynthetic pathway for membrane proteins, showing trafficking and its measurement with the present assay. As shown at arrow 1, a protein involved in trafficking in a eukaryotic cell normally moves from the ER (endoplasmic reticulum) to the Golgi apparatus; as shown at arrow 2, it then moves from the Golgi to the plasma membrane (PM); and as shown at arrow 3, it them moves to the endosome. There, agonist induced or basal mixing with endosomes and enzyme fragment complementation occurs (EFC) in the endosome. The EFC occurs by contact of the EA with the ED, which in this case is Prolink™ ED. As shown at numeral 4, the protein or protein fragment being studied ("target peptide") is provided with a small enzyme fragment which is present as a fusion with the target peptide as it travels through the trafficking pathway. A test compound is used to bind to the target peptide in the ER and thereby affect trafficking.
Figure 2:
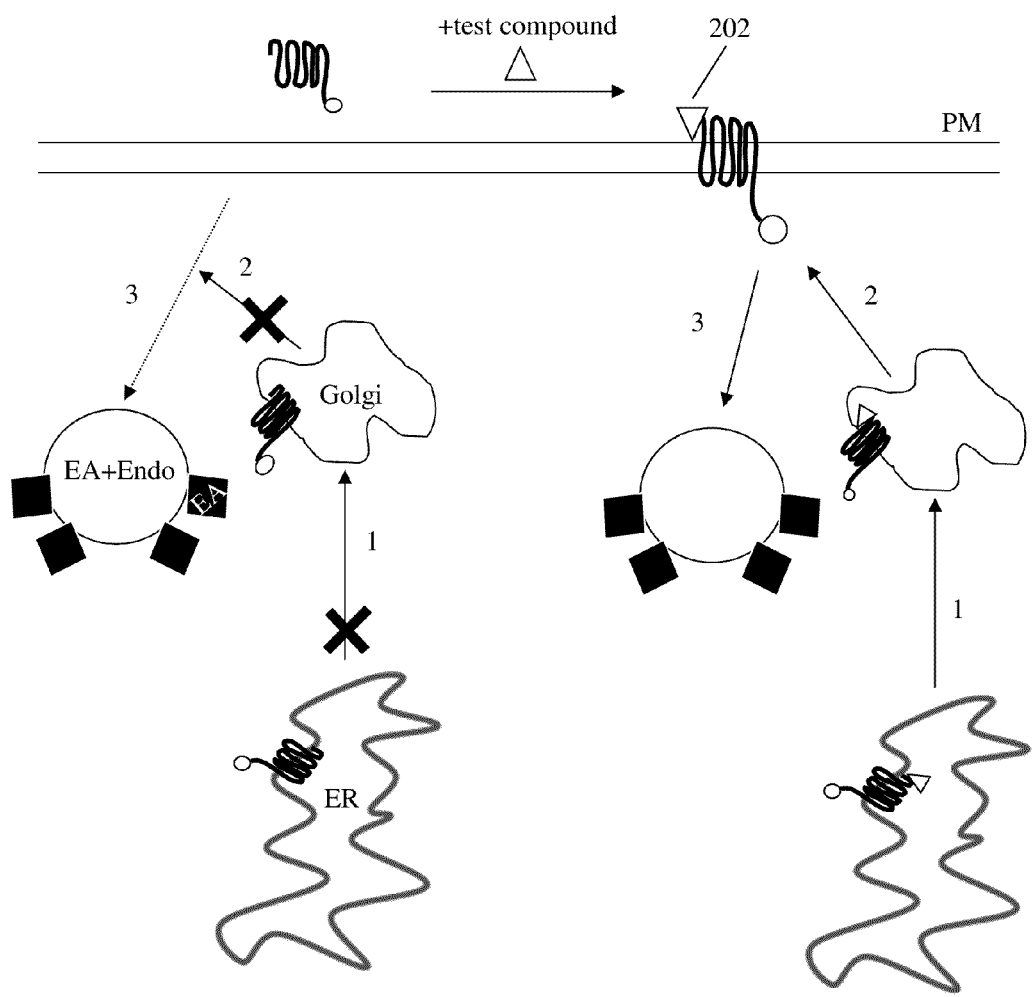
FIG. 2 is another diagrammatic representation of EFC monitoring of protein trafficking, showing movement where a GPCR tagged with a reduced affinity enzyme donor (202), termed "Prolink™," is contacted with a test compound. As in FIG. 1, the steps are trafficking from 1) ER to Golgi; 2) Golgi to PM; 3) agonist induced or basal mixing with the endosome, and complementation in the endosome. The addition of a test compound that binds to the target peptide (right side of figure) results in a high detectable signal upon complementation. In the case of a low signal, ER to Golgi transport is impaired (left side of figure) as the misfolded protein is retained in the ER, an instance of "abnormal trafficking" illustrated by a blocked arrow 1.
Figure 3:
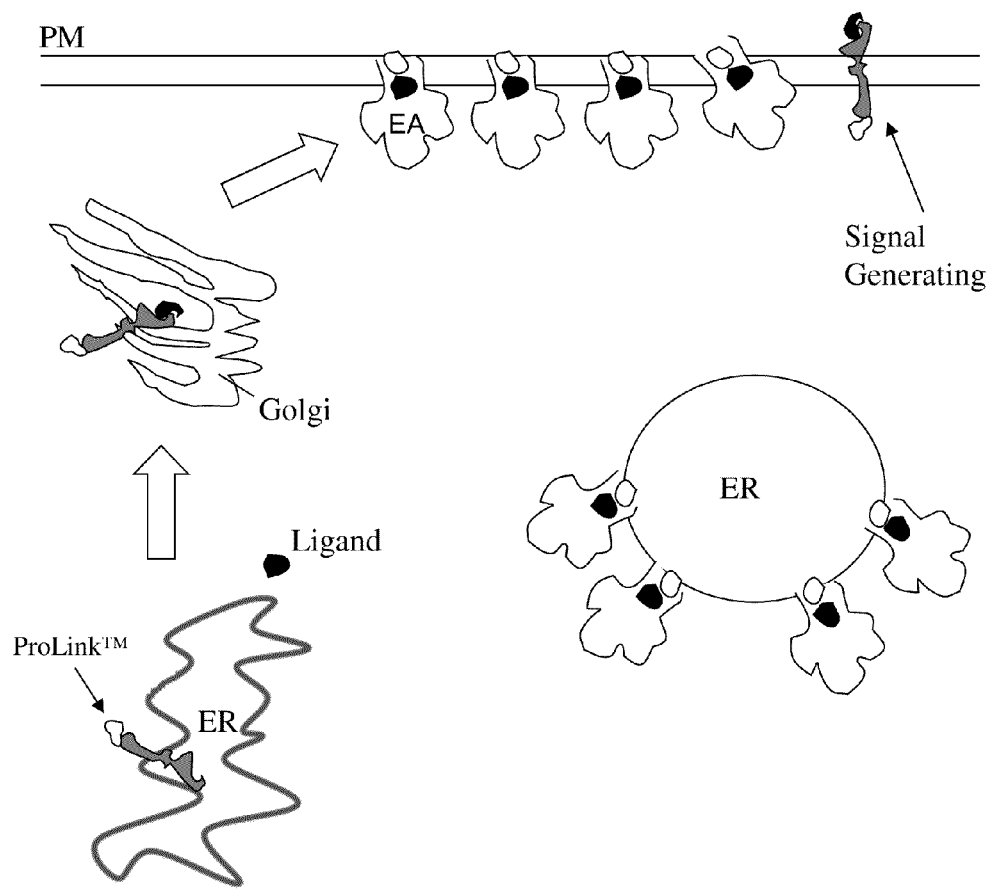
FIG. 3 is another diagrammatic representation of monitoring of protein trafficking through EFC, showing mis-folded hERG protein (potassium voltage-gated channel, subfamily H (eag-related), member 2, or "human Ether-à-go-go Related Gene" gene symbol KCNH2). Misfolding here results from a single-point mutation in KCNH2, and the mutant is tagged with an enzyme donor termed 'ProLink™'. The mis-folded protein gets trapped in the ER, resulting in low signal, that is, little enzyme complementation between ED and EA. The addition of a test compound, shown as "ligand," leads to binding to the target peptide in the ER and transport of protein from there to Golgi to PM and complementation with the EA at the plasma membrane.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification.

In accordance with the present invention there may be employed conventional molecular biology, microbiology, and recombinant DNA techniques within the skill of the art. Such techniques are explained fully in the literature. See, e.g. Maniatis, Fritsch & Sambrook, "Molecular Cloning: A laboratory Manual (1982); "DNA Cloning: A Practical Approach, "Volumes I and II (D. N. Glover ed. 1985); "Oligonucleotide synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide to Molecular Cloning" (1984).

It is noted that, as used herein and in the appended claims, the singular forms "a", "an", and "the" include plural referents unless the context clearly dictates otherwise. It is further noted that the claims may be drafted to exclude any optional element. As such, this statement is intended to serve an antecedent basis for use of such exclusive terminology as "solely", "only", and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the feature of any of the other several embodiments without departing from the scope or spirit of the present invention. Any recited method can be carried out in the order of events recited or in any other order which is logically possible.

For purposes of clarity, the following terms are defined below.

The term "protein trafficking" as used herein refers to the movement of proteins in eukaryotic cells through a pre-defined series of intracellular compartments. This includes movement of a translated protein from the rough endoplasmic reticulum to the Golgi apparatus via vesicles; modification and transport through the Golgi; packaging into vesicles at the trans Golgi network; and delivery of these vesicles to the final destination (e.g. lysosome or plasma membrane).

The term "peptide" as used herein refers to any polymer compound produced by amide formation between an α-carboxyl group of one amino acid and an α-amino group of another group. The term peptide includes full length proteins, protein fragments, mutated proteins, and peptides included in fusion proteins.

The term "fusion protein" as used herein refers to a protein created through genetic engineering from two or more proteins/peptides coding sequences joined together in a single polypeptide. In general, this is achieved by creating a "fusion gene", a nucleic acid that encodes and expresses the fusion protein. For example, a fusion gene that encodes a fusion protein may be made by removing the stop codon from a first DNA sequence encoding the first protein, then appending a DNA sequence encoding the second protein in frame. The resulting fusion gene sequence will then be expressed by a cell as a single fusion protein. Fusion proteins may include a linker (or "spacer") sequence which can promote appropriate folding and activity of each domain of the fusion protein. Fusion proteins may also include epitope tags for identification (e.g., in western blots, immunofluorescence, etc.) and/or purification. Non-limiting examples of epitope tags in current use include: HA, myc, FLAG, and 6-HIS.

The term "amino acid" as used herein refers to include not only the L-, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, ε-nicotinoyl-lysine, isonipecotic acid, tetrahydroisoquinoleic acid, α-aminoisobutyric acid, sarcosine, citrulline, cysteic acid, t-butylglycine, t-butylalanine, phenylglycine, cyclohexylalanine, β-alanine, 4-aminobutyric acid and the like. The amino acid sequences are given in one-letter code (A: alanine; R: arginine; N: asparagine; D: aspartic acid; C: cysteine; Q: glutamine; E: glutamic acid; G: glycine; H: histidine; I: isoleucine; L: leucine; K: lysine; M: methionine; F: phenylalanine; P: proline; S: serine; T: threonine; W: tryptophan; Y: tyrosine; V: valine; X: any residue). $NH_2$ refers to the free amino group present at the amino terminus of a polypeptide. COOH refers to the free carboxy group present at the carboxy terminus of a polypeptide in keeping with standard polypeptide nomenclature, (*J Biol. Chem.* 243 (1969), 3352-59) is used.

The term "vector" as used herein refers to a replicon, such a plasmid, phage or cosmid, to which another DNA segment may be attached so as to bring about the replication of the attached segment.

A cell has been "transformed" or "transfected" by exogenous or heterologous DNA when such DNA has been introduced inside the cell. The transforming DNA may or may not be integral (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lies or clones comprised of a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the genomic DNA in the genome of the source organism. In another example, heterologous DNA includes coding sequences in a construct where portions of genes from two different sources have been brought together so as to produce a fusion protein product. Allelic variations or naturally-occurring mutational events do not give rise to a heterologous region of DNA as defined herein.

The term "agonist" as used herein refers to a molecule or substance that binds to or otherwise interacts with a receptor or enzyme to increase activity of that receptor or enzyme. The term agonist as used herein encompasses both full agonists and partial agonists.

The term "antagonist" as used herein refers to a molecule that binds to or otherwise interacts with a receptor to block (e.g., inhibit) the activation of that receptor or enzyme by an agonist.

The term "receptor" as used herein refers to a protein normally found on the surface of a cell which, when activated, leads to a signaling cascade in a cell.

The terms "G protein coupled receptors" and "GPCRs" as used herein refer to all subtypes of the opioid, muscarinic, dopamine, adrenergic, adenosine, rhodopsin, angiotensin, serotonin, thyrotropin, gonadotropin, substance K, substrate P and substance R receptors, melanocortin, metabotropic glutamate, or any other GPCR known to couple via G proteins. This term also includes orphan receptors that are known to couple to G proteins, but for which no specific ligand is known. Examples of GPCRs which can be studied for trafficking using the methods of the invention include, but are not limited to, chemokine receptor 4 (CCCR4); cholinergic receptor, muscarinic 2 (CHRM2); corticotropin releasing hormone receptor 2 (CRHR2); G Protein-coupled receptor 44 (CRTH2); melanocortin 3 receptor (MC3R); opiod receptor mu-1 (OPRM1); somatostatin receptor 1 (SSTR1); somatostatin receptor 4 (SSTR4); histamine receptor H3 (HRH3); opiod receptor delta 1 (OPRD1); gonadotropin releasing hormone receptor (GnRHR); and beta-2 adrenergic receptor (ADRB2).

The term "ADRB2" as used herein refers to beta-2 adrenergic receptor, a member of the adrenergic receptor group of G-protein-coupled receptors that also includes alpha1A, alpha1B, alpha1D, alpha2A, alpha2B, alpha2C, beta1 and beta3. ADRB2 is a member of the G protein-coupled receptor superfamily. This receptor is directly associated with one of its ultimate effectors, the class C L-type calcium channel Ca(V)1.2. This receptor-channel complex also contains a G protein, an adenylyl cyclase, cAMP-dependent kinase, and the counterbalancing phosphatase, PP2A. The assembly of the signaling complex provides a mechanism that ensures specific and rapid signaling by this G protein-coupled receptor. The gene ADRB2 is intronless. Different polymorphic forms, point mutations, and/or downregulation of this gene are associated with nocturnal asthma, obesity and type 2 diabetes.

The term "CHRM4" as used herein refers to muscarinic cholinergic receptors which belong to the larger family of G protein coupled receptors. The receptors bind to acetylcholine and induce cellular responses such as adenylate cyclase inhibition, phosphoinositide degeneration and potassium channel modulation. The sequence is given at UniProt entry P08173

The term "hERG" as used herein refers to a gene (KCNH2) that codes for a protein known as Kv11.1 potassium ion channel. This ion channel is best known for its contribution to the electrical activity of the heart that coordinates the heart's beating. The sequence is given at UNiProt entry Q6U279.

The term "sub-cellular compartment localized" as used herein refers to a molecule (e.g., a peptide, protein, etc.) that, when present in a cell, is found predominantly associated with a specific sub-cellular compartment. Sub-cellular compartments of interest include, but are not limited to lysosomes, endosomes, the Golgi apparatus, the endoplasmic reticulum, the nucleus, chloroplast and mitochondria. A sub-cellular compartment localized molecule may be naturally occurring or one that has been engineered (e.g., genetically engineered) to predominantly associate with the sub-cellular compartment of interest. Localization is accomplished by means of a peptide sequence that is known in the cell to be part of a localized protein and that directs the protein to its destination compartment or organelle. A database listing protein localizations may be found online at rostlab.org under the name "LocDB." In the working examples, the endofin FYVE domain is used; other FYVE domain proteins are known; see Seet et al. "Endofin, an endosomal FYVE domain protein," J. Biol. Chem. 276:42445-54 (2001).

The term "optional" or "optionally" as used herein refers to mean that the subsequently described circumstance may or may not occur, so that the description includes instances where the circumstance occurs and instances where it does not.

Overview

The present methods and compositions provide systems of identifying and monitoring protein trafficking as well as its progression through various components of trafficking pathway. Membrane proteins such as GPCRs are subject to a "quality control" process to ensure that they are properly folded and formed before being inserted into the plasma membrane. Typically, the life of GPCRs begins at the ER where they are synthesized, folded and assembled. Properly folded receptors are recruited and packaged into ER-derived COPII-coated vesicles. Transport vesicles carrying cargo receptors then migrate from the ER to the ER-Golgi intermediate complex (ERGIC), the Golgi apparatus and the trans-Golgi network (TGN). During their migration, receptors undergo post-translational modifications (e.g. glycosylation) to attain mature status. Mature receptors then move from the TGN to their functional destination at the plasma membrane. Upon stimulation by their ligands, GPCRs at the plasma membrane may undergo internalization which involves phosphorylation of the receptors by G protein receptor kinases, and subsequent binding of phosphorylated receptors to arrestins. Arrestins function as adaptor proteins recruiting components of the transport machinery to the clathrin-coated pits and initiating formation of the early endosome. Internalized receptors in the endosome are sorted to the recycling endosome for return to the plasma membrane or to the lysosome for degradation. The balance of this dynamic intracellular trafficking (i.e. export, endocytosis and degradation) dictates the level of receptor expression at the plasma membrane, which in turn influences the magnitude of the cellular response to a given signal. Various conditions may result in abnormal protein trafficking, such as improper protein folding, or post-translational modification in the protein being trafficked, or other mutations in such protein.

Of particular importance in the present methods is the ER. The ER quality control scrutinizes newly synthesized proteins entering the secretory pathway and assures that only correctly folded proteins and fully assembled protein complexes ultimately reach their site of action within the cell. Even subtle mutations that would not dramatically affect protein function can lead to ER retention of the mutant protein. This is exemplified in many important human diseases. For example, mutations that produce minor changes in the cystic fibrosis transmembrane conductance regulator (CFTR), alpha1-antitrypsin and V2-vasopressin receptor (V2R) have been shown to be the underlying cause for cystic fibrosis and some forms of emphysema and nephrogenic diabetes insipidus, respectively.

There can be many reasons which lead to proteins being retained in the endoplasmic reticulum (termed herein "abnormal trafficking") including but not limited to improper conformation, lack of cellular processing including proteolytic cleavage or carbohydrate modification, lack of specific binding proteins, or the specific retention due to binding of the target peptide. Several studies have indicated that trafficking to the target site can be restored by binding of the target peptide that is retained in the ER, with a compound ('test compound'). This compound can be comprised of a protein or group of proteins, peptide, small molecule, chemical compound or the like. Alternatively, the compound can interact with the protein that retains the target within the ER thus causing release of the target to progress further downstream to its target destination. The target peptide can also be released from the ER through cleavage by a protease, or cleavage of the ER-retaining protein.

Described below is a detection system to monitor progression of the target peptide through the trafficking pathway using reduced affinity enzyme fragment complementation. Methods and compositions for monitoring the progression of the target peptide through the trafficking pathway are provided using a reduced affinity β-galactosidase complementation reporter system. Systems and kits are also provided for use in practicing embodiments of the methods. Before the present invention is described in great detail, it is to be understood that this invention is not limited to particular embodiments described, as such may vary.

The present invention employs enzyme fragment complementation (EFC) where one fragment of a β-galactosidase enzyme (preferably "the enzyme donor" (ED)) is fused to a protein, known as the "target" protein or "target peptide" that moves from a first cellular compartment to a destination cellular compartment, and a second fragment, preferably the "enzyme acceptor" (EA), is fused to a protein localized in a selected destination cellular compartment. In certain aspects, the present invention exploits the ability of the endoplasmic reticulum ("ER") to act as a form of "traffic control" that can be modulated by the binding of certain molecules to the target peptide, causing release of the target peptide from the ER, eventually moving to the destination compartment where the EA is localized. For example, the EA is localized to the endosome as a destination compartment, by tagging an endosomal protein with an EA. The endosomal protein will contain an FYVE domain. The FYVE domain is a conserved sequence present in more than 30 proteins in species from yeast to mammals. The major functional role of the FYVE domain proteins characterized thus far is membrane trafficking. The FYVE domain is a protein domain also known as the FYVE zinc finger, named after four proteins that it has been found in: Fab1, YOTB/ZK632.12, Vac1, and EEA1. The FYVE domain has been shown to bind two zinc ions, and has eight potential zinc coordinating cysteine positions. Many members of this family also include two histidines in a motif R+HHC+XCG, where + represents a charged residue and X any residue. FYVE-type domains are divided into two known classes: FYVE domains that specifically bind to phosphatidylinositol 3-phosphate in lipid bilayers and FYVE-related domains of undetermined function. Those that bind to phosphatidylinositol 3-phosphate are often found in proteins targeted to lipid membranes that are involved in regulating membrane traffic. Most FYVE domains target peptides to endosomes by binding specifically to phosphatidylinositol-3-phosphate at the membrane surface. Consensus sequences may be obtained from http(colon slash slash)smart.embl-heidelberg.de/smart/show_info.pl.

The present methods include the use of GPCRs that have been modified to either omit a domain needed for ER export, or modified to contain a signal that causes retention in the ER. This would result in an ER-Bound GPCR that is retained in the ER until it is bound to a compound that acts as a chaperone and causes the mutant GPCR to be released from the ER.

As another example, certain receptors have been shown to only traffic to the cell surface in the presence of a second protein. For example GABBR1 (Gamma-aminobutyric acid [GABA] B receptor, 1) only locates to the plasma membrane in the presence of GABBR2 (Gamma-aminobutyric acid (GABA) B receptor, 2). Thus by using the presently disclosed methods and materials, GABBR1 binding partners can be identified using the interaction with a third protein. In this case the target peptide would be fused to an enzyme donor such as ProLink™ and expressed in a cell background that expresses EA at the endosome or plasma membrane. A third protein, in this case GABBR2 or a set of potentially interacting proteins would then be introduced. Each resulting cell line would then be compared to the parental in terms of the amount of complemented enzyme. If the potentially interacting protein was able to bind the target and enhance its plasma membrane localization then a gain of signal would be detected.

Chemical or pharmacological manipulation can rescue misfolded proteins and lead to their proper translocation. As an example, the addition of a cell permeable vasopressin 2 receptor (V2R) antagonist to a subset of mutant V2Rs previously shown to accumulate in the ER resulted in proper folding, ER exit, correct targeting to the cell surface, and functional rescue of receptor activity of the mutant proteins. As another example, the delta opioid receptor increases its trafficking to the cell surface in the presence of a ligand. That is, as reported in Petaja-Repo et al., "Ligands act as pharmacological chaperones and increase the efficiency of delta opioid receptor maturation," EMBO Journal (2002) 21, 1628-1637, only a fraction of newly synthesized delta opioid receptors leave the ER and reach the cell surface, the rest being degraded by proteasomes. Membrane-permeable opioid ligands facilitate maturation and ER export of the receptor, thus acting as pharmacological chaperones. Additional mutant 7-transmembrane receptors known to have altered trafficking properties that result in human disease, and for which molecular chaperones have been identified, include rhodopsin, the sulfonylurea receptor 1 (SUR1), smoothened, and the gonadotropin-releasing hormone receptor (GnRHR).

Thus, the present methods also find utility in helping to identify "chemical chaperones" which may be useful in treating diseases which involve impaired trafficking of mutant proteins. A protein may be able to adopt a functionally competent conformation even if it is normally retained by the ER quality control. This is demonstrated by the ability of the so-called chemical chaperones, such as glycerol, trimethylamine-N-oxide and dimethyl sulfoxide, to rescue targeting and function of the affected protein. In line with these findings are observations on the V2R, a member of the G protein-coupled receptor (GPCR) superfamily. Two non-peptidic V2R antagonists were able to functionally rescue several receptor mutants that were normally retained in the ER (Morello J-P et al. (2000). Pharmacological chaperones rescue cell-surface expression and function of misfolded V2 vasopressin receptor mutants. J Clin Invest, 105, 887-895).

General Methods and Materials
Destabilizing Protein Alterations Causing Misfolding As described above, the present methods may take advantage of a number of known mutations in proteins where misfolding and retention in the ER results. Cell membrane receptors and ion channels are exemplified below.

Exemplified is a mutation in the G protein coupled receptor ADRB2, which is the adrenergic, beta-2-, receptor. A full sequence is given at UniProt entry P07750, where the mutated W158 can be seen to be present in a transmembrane region. This region contains substantial sequence homology to a number of other GPCRs, were similar mutations may be expected to also cause ER retention. This structural and functional (cholesterol binding) homology is described in further detail in US PGPUB US 2011/0130543 entitled "Cholesterol consensus motif of membrane proteins," by Stevens et al., published Jun. 2, 2011. This sequence is RVIILMV WIVSGLTSFLPIQMHWY (SEQ ID NO: 1) where the residue that is mutated (e.g. to A) is underlined. Similar sequences exist in the human dopamine receptor D5 and D1, ubiquitin specific peptidase 52, G protein-coupled receptor PGR28, beta-3-adrenergic receptor, 5-hydroxytryptamine-4 receptor, 5-HT4 receptor, etc. Thus a variety of GCPR misfolding mutations will also find use in the present assays.

In some cases, one may use the present methods to assay for a decrease in protein trafficking. For example, opioid receptors (a class of GPCR) may become constitutively active. Mutations may be introduced to cause constitutive activity and compounds tested for causing a destabilizing misfolding and retention in the ER. See for details on opioid receptor trafficking, Petäjä-Repo U E, Hogue M, Laperrière A, Walker P, Bouvier M: "Export from the endoplasmic reticulum represents the limiting step in the maturation and cell surface expression of the human delta opioid receptor," J Biol Chem 2000, 275:13727-13736 and Brillet et al. "Enhanced spontaneous activity of the mu opioid receptor by cysteine mutations: characterization of a tool for inverse agonist screening," BMC Pharmacology 2003, 3:14.

Other membrane proteins, such as connexins (gap junction proteins), exhibit such misfolding and ER retention. Dhaunchak et al. "A common mechanism of PLP/DM20 misfolding causes cysteine-mediated endoplasmic reticulum retention in oligodendrocytes and Pelizaeus-Merzbacher disease," Proc. Nat. Acad. Sci. 104:17813-17818 reports on the molecular consequences of missense mutations in the PLP1 gene, encoding the major integral membrane protein of CNS myelin. Numerous PLP1 missense mutations cause ER retention and oligodendrocyte death in Pelizaeus-Merzbacher disease (PMD), whereas null mutations of the same gene are well tolerated and allow myelination. Misfolding mutations in the immunoglobin light chain protein AL-09 are also known to cause amyloidosis (See J Biol Chem. 2008 Nov. 7; 283(45):30950-6. Epub 2008 Sep. 2, "Structural insights into the role of mutations in amyloidogenesis.")

In addition, given the present disclosure, one may generate mutations in proteins of interest. A receptor, ion channel or enzyme having a known misfolding mutation may serve as a template for introducing a mutation into a structurally similar protein. In preparing the present fusion proteins, the target peptide need not be used in its entirety. It may be present as a fragment, as long as the peptide is subject to altered trafficking in the same manner as the full length protein.

Functional Rescue

It has now been found that compounds that bind to misfolded proteins that are retained in the ER can be contacted with molecules, including small nonpeptide molecules, that can serve as molecular templates promoting correct folding and, importantly, that this effect can be monitored by the present assay. Conn et al. "G Protein-Coupled Receptor Trafficking in Health and Disease: Lessons Learned to Prepare for Therapeutic Mutant Rescue in Vivo," Pharmacol. Rev. 59(3): 225-250 (2007) describe such rescue and suggest that such rescue might have therapeutic applications. The small molecules that cause the rescue are termed "pharmacochaperones", and the authors constructed a large number of (non-naturally occurring) mutations, including deletions and truncations, in the human and rodent GnRH receptors and found that the vast majority can be rescued by pharmacological means.

GPCRs

GPCRs, exemplified herein, follow the regular trafficking pathway (ER-Golgi-cell-surface transport), get assembled and reach the target site in the plasma membrane. A number of GPCR mutations are known to cause misfolding and retention in the ER.

For example, if the C-terminal segment (also known as tail segment) is mutated/modified-ER will recognize it as an improper conformation and will retain the protein. If there is a modification of one or more cysteine residues in tail segment—the modified GPCR will be treated as a misfolded protein and will be retained in ER.

A number of diseases are caused by receptor misfolding which makes it important to study GPCR trafficking and cell surface membrane expression.

| GPCR | disease/abnormality |
|---|---|
| Rhodospin | Retinitis pigmentosa |
| V2R | Nephrogenic diabetes inspidus |
| GnRHR | Hypogonadotropic hypogonalism |
| CaR | Familial hypocalciuric hypercalcemia |
| PTH/PTHrP | Jansen metaphyseal chondrodysplasia |
| LHR | Male pseudohermaphroditism; hypergonadotropic hypogonadism |
| FSHR | Ovarian dysgenesis |
| ACTHR | Familial ACTH resistance |

For example, GPCRs normally require a post translational lipidation (e.g. palmitic acid attachment to a cysteine) in order to be inserted into the plasma membrane. By removing the portion of the GPCR that is responsible for this, e.g. helix 8, the GPCR will be retained in the ER. However, binding of a test compound to the GCR will cause it to be released from the ER and traffic to the plasma membrane and the endosome. In this way, the present methods may be adapted to a variety of GPCRs. The present methods detect any manner of binding to the target peptide. They can be used to "de-orphanize" orphan GPCRs. Antagonists will cause GPCR trafficking without the need for an agonist control.

Other mutated/altered GPRRs are known to be involved in human disease. Such mutated GPCRs can also be prepared as target peptides and utilized in the present methods. Angiotensis II type I GPCR (AT1R)-AT1R polymorphism such as A1166C is associated with hypertension (Bonnardeaux, A., Davies, E., Jeunemaitre, X., et al., 1994 Angiotensin-II type-1 receptor gene polymorphisms in human essential-hypertension. Hypertension. 24, 63-69), left ventricular hypertrophy (Takami, S., Katsuya, T., Rakugi, H., et al., 1998 Angiotensin II type 1 receptor gene polymorphism is associated with increase of left ventricular mass but not with hypertension. Am. J. Hypertens. 11, 316-321), coronary heart disease, myocardial infarction (Tiret, L., Bonnardeaux, A., Poirier, O., et al., 1994 Synergistic effects of angiotensin-converting enzyme and angiotensin-II type-1 receptor gene polymorphisms on risk of myocardial-infarction. Lancet. 344, 910-913) and progression of diabetic nephropathy (Wang, J. G., and Staessen, J. A., 2000 Genetic polymorphisms in the renin-angiotensin system: relevance for susceptibility to cardiovascular disease. Eur. J. Pharmacol. 410, 289-302; Tomino, Y., Makita, Y., Shike, T., et al., 1999 Relationship between polymorphism in the angiotensinogen, angiotensin-converting enzyme or angiotensin II receptor and renal progression in Japanese NIDDM patients. Nephron. 82, 139-144).

Mutated form of GPCR-adrenergic receptors Pro64Gly variant form of β3-adrenergic is associated with some cases of obesity (Strosberg, A. D., 1997 Structure and function of the beta (3)-adrenergic receptor. Annu. Rev. Pharmacol. Toxicol. 37, 421-450)

Variants of β2 adrenergic receptor Thr 164Ile polymorphism is associated with increased severity of congestive heart failure.

Arg16Gly is also associated with reduced lung function, familial nocturnal asthma CCK (Cholecytokinin)-abnormal expression of CCKβ/gastric receptor has been associated with colon cancer Protease activated receptors (PARs)-a Phe240Ser variant of the receptor can disrupts receptor activation by proteolysis.

Ion Channels

The presently disclosed methods and materials can also be used to study ion channels, e.g., hERG is a gene that codes for a protein known as $k_v11.1$ potassium ion channel and is best known for its contribution to the electrical activity of the heart that coordinates the heart's beating. Certain factors are known that affect the trafficking of cell membrane proteins (e.g. receptors) to the cell surface. For example, single-point mutation in KCNH2 results in a misfolded hERG protein and as a result of this mutation, proteins gets trapped in ER. Addition of a compound leads to the stabilization and transport of the protein from the ER to membrane. Thus the target peptide is fused to the first fragment of complementation assay and the second fragment is at membrane. Upon the addition of compound the protein will exit the ER scrutiny and will follow the trafficking path further. The target peptide will then encounter the second fragment and thus an increase in signal will be observed which can be detected using a chemiluminescent/fluorescent substrate.

Thus, the studies to monitor the trafficking of ion channels can be an important target for drug discovery studies.

The present method also includes the use of ion channels in which a mutation/insertion/deletion has been introduced which would cause retention of the protein in the ER. The addition of a compound thus acts as a chaperone and leads to the export of protein from the ER and follows the path of maturation.

Ion channel expression regulation begins at the level of gene transcription and mRNA stability. Messenger RNA is exported from the nucleus to the cytoplasm where ribosomal proteins translate coding regions into polypeptide chains. The peptide is then inserted into the ER where the maturation and formation of proper tertiary structure takes place. After folding and assembly, the protein is transported out of the ER through vesicles budding where it travels along cytoskeleton element to the ER-Golgi intermediate complex. Thus a protein must attain a correct tertiary structure to function properly. Thus, mutation/deletion/insertion on protein sequence can lead to improper protein folding and the protein will be retained in the ER and will not follow the path of maturation to function properly. However, introduction of a compound will help the protein to old properly and exit from the ER and follow the maturation pathway. In this manner, the present methods may be employed for a variety of ion-channels.

TGF-Beta Receptors

Another class of proteins which may be used in the present assay is the TGF-beta family of receptors. Li et al. "Bone Morphogenetic Protein Type II Receptor Mutations Causing Protein Misfolding in Heritable Pulmonary Arterial Hypertension," Proc. Am. Thorac. Soc. 7:395-390 (November 2010) discloses mutations in the in the gene encoding the bone morphogenetic protein type II receptor (BMPR-II), a receptor for the transforming growth factor-β/BMP superfamily. Among the many mutations identified, some involve substitution of cysteine residues in the ligand-binding domain or the kinase domains of BMPR-II. These mutants are characterized by retention within the endoplasmic reticulum. Bone morphogenetic proteins (BMPs) are the largest group of cytokines within the TGF-β superfamily.

In the ligand-binding domain of BMPR-II the 10 cysteine residues form 5 disulfide bonds. A feature common to all the cysteine substituted mutations studied is the retention of mutant BMPR-II protein in the endoplasmic reticulum (ER). Cysteine-substituted BMPR-II mutants retained within the ER also prevent normal trafficking of BMP type I receptors, but not wild-type BMPR-II.

The family of TGF beta receptors are single pass serine/threonine kinase receptors. Further details on the TGF (transforming growth factor) beta receptors may be found, e.g. at Doré Jr, J. J.; Edens, M.; Garamszegi, N.; Leof, E. B. (1998).

"Heteromeric and homomeric transforming growth factor-beta receptors show distinct signaling and endocytic responses in epithelial cells". The Journal of biological chemistry 273 (48): 31770-31777

Monitoring the Target Peptide Fusion Protein

Embodiments of the invention provide methods for monitoring the progression of the target peptide (i.e. the protein being monitored) as it follows the trafficking pathway in a cell. Embodiments of the method include determining whether said target peptide encountered the sub-cellular compartment localized molecule in a cell. In one embodiment, 1) the target peptide is fused to the first fragment of a reduced-affinity enzyme complementation reporter system and 2) the localization of the second fragment of a reduced-affinity enzyme complementation reporter system is at a sub-cellular site which is located within the trafficking path of the target peptide.

As the target peptide is induced to traffic further towards the site of action then it would encounter the second fragment of a reduced-affinity enzyme complementation reporter system en route. The increase in localization will then result in an increase in reporter enzyme and the result of the evaluation is employed to determine whether the target peptide has encountered the said sub-cellular compartment in the trafficking pathway. Functionality of the enzyme can be detected using a chemiluminescent or fluorescent substrate.

In one embodiment 1) the target peptide is fused to the first fragment of a reduced-affinity enzyme complementation reporter system that is retained within a specific sub-cellular compartment and 2) the localization of the second fragment of a reduced-affinity enzyme complementation reporter system is also at the same sub-cellular compartment. If the target peptide traffic further in the path, it will result in a decrease in reporter enzyme complementation and the result of the evaluation is employed to determine whether the target peptide has moved further in the trafficking pathway.

Reduced-Affinity Complementation Reporter System

Aspects of the methods include the use of a reduced-affinity enzyme complementation reporter system which is extensively described in the aforementioned reference, U.S. Pat Appln. No. 20100285451, "Detection of sub-cellular compartment localization of a molecule using a reduced affinity enzyme complementation reporter system, which is also specifically incorporated by reference as if set forth in its entirety herein, as set forth at the end of the specification. Typically reduced affinity will mean an affinity that is at least 20% lower, or 30% lower or 50% lower than an affinity of a native fragment for the same binding fragment.

Signal-to-Noise Ratio

Embodiments of the reduced-affinity enzyme complementation reporter systems are characterized by providing high signal-to-noise ratio.

In the present invention, the reduced-affinity enzyme complementation systems provides for a first detectable signal when the enzyme subunits are present in or on separate sub-cellular compartment that is significantly less than a second detectable signal that is detected when the enzyme subunits are present in the same sub-cellular organelle.

Reduced Affinity Binding Fragments

The enzyme fragments of enzyme complementation reporter system as in the present presently disclosed methods and materials have sufficiently low-binding affinity for each other such that they exhibit reversible binding for each other and are still capable of associating with each other and generating a detectable signal when present within or on a sub-cellular compartment. The enzyme fragments of enzyme complementation reporter system having low-binding affinity can be generated using a number of different approaches which have been explained in U.S Patent Appln. Serial No. 20100285451, Pub. Date Nov. 11, 2010 (incorporated herein by reference) as well as U.S. Patent Appln Ser. No. 11/132,764 filed on May 18, 2005 for a review employed with a high-affinity β-galactosidase complementation reporter system (incorporated herein by reference). The enzyme fragments of reduced affinity as in the present methods and materials include any reduced binding affinity fragments, which are capable of associating to produce a detectable signal. Embodiment of the method include that the enzyme fragments as in the present presently disclosed methods and materials are protein which are capable of associating and are capable, when associated, of catalyzing a reaction which produces a product which can be estimated directly or indirectly.

The wild-type $E.\ coli$ β-galactosidase forms the basis for the present reduced-affinity enzyme complementation reporter system. The wild-type $E.\ coli$ β-galactosidase is encoded by the $E.\ coli$ lacZ gene. The enzyme of interest as described above is not limited to but the enzyme fragments can also be derived from β-glucuronidase (GUS), β-lactamase, alkaline phosphatase, peroxidase, chloramphenicol acetyltransferase (CAT), cre-recombinase and luciferase.

Measurement of Enzyme Activity

A range of methods are available to measure the enzyme activity of β-galactosidase which include live cell flow cytometry and histochemical staining with the chromogenic substrate 5-bromo-4-chloro-3-indolyl β-D-galactopyranoside (X-Gal). see e.g., Nolan et al., Proc. Natl. Acad. Sci., USA, 85: 2603-2607 (1988); and Lojda, Z., Enzyme Histochemistry: A laboratory Manual, Springer, Berlin, (1979).

Characteristics of the Enzyme Fragments

The enzyme fragments as used in the present presently disclosed methods and materials are β-galactosidase fragments, where the fragments may have amino acid sequences found in their corresponding wild-type β-galactosidase molecule or have sequences that are variants of sequences found in their wild-type β-galactosidase molecules. In certain embodiments, the enzyme complementation system is made up of two or more β-galactosidase fragments or variants thereof (e.g., an α or ω fragment) or may include more than two β-galactosidase fragments (e.g., an α, μ and ω fragment).

By determining the activity level of the signal producing system, a conclusion can be drawn whether the target peptide is moving further in the trafficking pathway The present methods may employ a variant of native N-terminal β-galactosidase peptide, such that the peptide has an amino acid sequence that is found in the N-terminal region of a wild-type β-galactosidase protein, e.g., a sequence that starts within about 10 residues of the N-terminus, such as within about 5 residues of the N-terminus of a wild-type β-galactosidase protein. The fragment may be about 60 amino acids or less in length, such as about 55 amino acids in length or less, including about 50 amino acids or less in length, e.g., 49 amino acids or less in length etc.

The sequence variation may be one or more of an insertion, deletion or substitution, e.g., in the form of point mutation. The variant of minimal N-terminal β-galactosidase peptides may have a single variation (such as insertion, deletion, point mutation) or two or more different variations (such as two or more point mutations) etc. In certain embodiments, the first fragment of β-galactosidase has a binding affinity for the second fragment of β-galactosidase (described in greater detail below) which is less than the binding affinity of a fragment having the complete sequence from amino acid residue 3 to 92 (e.g., as described in Langley et al., J. Biol.

Chem. (1975) 250: 2587-2592) of wild-type E. coli β-galactosidase for a second fragment of β-galactosidase, e.g., where the binding affinity is less than the wild-type fragment for the second fragment of β-galactosidase.

In certain embodiments, any variation in the sequence occurs in a region of the β-galactosidase fragment that, upon complementation of the fragment with the second fragment of the complementation system, is in a "buried" location within the second β-galactosidase fragment. In certain embodiments, this domain includes the sequence found from amino acid residue 29 to 41 of the wild-type sequence, and therefore the fragment includes a variation in this region, e.g., from amino acid residues 29 to 41, such as from amino acid residue 31 to 41. For example, where the variations are point mutations the variant may include one or more point mutations at any of amino acid residues 29 to 41, such that one or more of these 13 amino acid residues may be substituted, including 2 or more, 3 or more, 4 or more etc., of these amino acid residues may be substituted. Specific reduced affinity amino acid point mutations of interest include, but are not limited to: H31 (e.g., H31R); F34 (e.g., F34Y); E41 (e.g., E41Q); and N39 (e.g., N39Q, N39D).

Exemplary minimal N terminal, α peptide, sequences include:

lication no. 2007/0275397 entitled "Detection of molecular interactions using a reduced affinity enzyme complementation reporter system, both of which references are incorporated herein as stated at the end of the specification. The mutated ED will desirably have less than about 0.5, but at least about 0.1, of the activity of the wild-type sequence in the assay of interest or an analogous assay. For increasing affinity between the ED and EA, EDs will be used and free of mutations from the wild-type sequence.

In certain embodiments the ED will be a low affinity (~30 fold lower affinity for the enzyme acceptor) peptide termed ProLink™ ED having the sequence:

```
                                               SEQ ID NO. 7
DSLAVVLQRRDWENPGVTQLNRLAARPPFASWRNSEEARTDR
```

The second β-galactosidase fragment may be any fragment that is capable of interacting with the first fragment of β-galactosidase to provide for detectable β-galactosidase activity. The second β-galactosidase fragment may include a major portion of the β-galactosidase enzyme, corresponding to greater than about 60% greater than about 80%, or greater than about 90% of the full-length β-galactosidase enzyme,

```
                                                          SEQ ID NO. 1
(H31R)
MGVITDSLAVVLQRRDWENPGVTQLNRLAARPPFASWRNSEEARTDRPSQQL

SEQ ID NO: 3
(F34Y)
MGVITDSLAVVLQRRDWENPGVTQLNRCAAHPPYASWRNSEEARTDRPSQQL

SEQ ID NO. 4
(E41Q)
MGVITDSLAVVLQRRDWENPGVTQLNRLAAHPPFASWRNSQEARTDRPSQQL

SEQ ID NO. 5
(N39D)
MGVITDSLAVVLQRRDWENPGVTQLNRLAAHPPFASWRDSEEARTDRPSQQL

SEQ ID NO. 6
(Truncated)
MGVITDSLAVVLQRRDWENPGVTQLNRLAAHPPFASWRDSEEA
```

In the above sequences the indicated substitution is underlined. In embodiments where the first fragment is a variant minimal N-terminal β-galactosidase fragment, as reviewed above, the first fragment may be used in conjunction with one or more additional fragments as reviewed above. In certain embodiments, the reporter system is made up of a first and a second β-galactosidase fragment.

The first fragment of β-galactosidase (enzyme donor, or "ED") may have the naturally occurring sequence or a mutated sequence. Of particular interest are small fragments of from about 36 to 60, more usually not more than about 50, amino acids. Desirably, the ED has a low affinity for the large fragment of β-galactosidase (enzyme acceptor, or "EA"), so that there is little complexation between the large and small fragments in the absence of recruitment of the complementing β-galactosidase fragment to endosomes, that is, the signal observed with the small fragment is at least about 50%, more usually at least about 70%, less than the signal observed with the commercially available fragment of 90 amino acids, when the two fragments are combined in the absence of fusion with other proteins. For further description of high affinity β-galactosidase enzyme donor fragments, see U.S. Pat. No. 7,135, 325 entitled "Short enzyme donor fragments". For further description of mutated EDs, see U.S. patent application pub-based on the molecular weight of the full-length β-galactosidase enzyme. In certain embodiments, the second fragment of β-galactosidase is a deletion mutant that is missing amino acid 11-41 of the wild-type E. coli β-galactosidase protein (e.g., as described in Langley et al., Proc. Natl. Acad. Sci. USA (1975) 72: 1254-1257), which fragment is known as M15 acceptor or ω fragment. Other specific acceptors (i.e., ω-fragments) of interest include, but are not limited to: the M112 dimer, a deletion of amino acids 23-31 within β-galactosidase (Lin, Villarejo and Zabin, 1970, Biochem. Biophys. Res. Common. 40: 249; Celeda and Zabin, 1979, Biochem, 18: 404; Welphy, Fowler and Zabin, 1981, J. Biol. Chem. 256-6804; Langley et al., 1975, Proc. Nat'l. Acad. Sci. USA 72, 1254). One exemplary ω peptide sequence is set forth below

```
                                                    (SEQ ID NO. 8)
MGVITDSLAVVARTDRPSQQLRSLNGEWRFAWFPAPEAVPESWLECDLPE

ADTVVVPSNWQMHGYDAPIYTNVTYPITVNPPFVPTENPTGCYSLTFNVD

ESWLQEGQTRIIFDGVNSAFHLWCNGRWVGYGQDSRLPSEFDLSAFLRAG

ENRLAVMVLRWSDGSYLEDQDMWRMSGIFRDVSLLHKPTTQISDFHVATR
```

```
FNDDFSRAVLEAEVQMCGELRDYLRVTVSLWQGETQVASGTAPFGGEIID

ERGGYADRVTLRLNVENPKLWSAEIPNLYRAVVELHTADGTLIEAECDVG

FREVRIENGLLLLNGKPLLIRGVNRHEHHPLHGQVMDEQTMVQDILLMKQ

NNFNAVRCSHYPNHPLWYTLCDRYGLYVVDEANIETHGMVPMNRLTDDPR

WLPAMSERVTRMVQRDRNHPSVIIWSLGNESGHGANHDALYRWIKSVDPS

RPVQYEGGGADTTATDIICPMYARVDEDQPFPAVPKWSIKKWLSLPGETR

PLILCEYAHAMGNSLGGFAKYWQAFRQYPRLQGGFVWDWVDQSLIKYDEN

NPWSAYGGDFGDTPNDRQFCMNGLVFADRTPHPALTEAKHQQQFFQFRLS

GQTIEVTSEYLFRHSDNELLHWMVALDGKPLASGEVPLDVAPQGKQLIEL

PELPQPESAGQLWLTVRVVQPNATAWSEAGHISAWQQWRLAENLSVTLPA

ASHAIPHLTTSEMDFCIELGNKRWQFNRQSGFLSQMWIGDKKQLLTPLRD

QFTRAPLDNDIGVSEATRIDPNAWVERWKAAGHYQAEAALLQCTADTLAD

AVLITTAHAWQHQGKTLFISRKTYRIDGSGQMAITVDVEVASDTPHPARI

GLNCQLAQVAERVNWLGLGPQENYPDRLTAACFDRWDLPLSDMYTPYVFP

SENGLRCGTRELNYGPHQWRGDFQFNISRYSQQQLMETSHRHLLHAEEGT

WLNIDGFHMGIGGDDSWSPSVSAEFQLSAGRYHYQLVWCQK.
```

Aspects of the invention include the use of the reduced-affinity reporter systems described above to monitor the target peptide as it follows the trafficking pathway.

Reporter Subunits

The reporter subunits are stably associated to the molecule of interest and the sub-cellular localized molecule. In certain embodiments, the stable association is either directly or via a linker, where the linkage may or may not be a covalent linkage. For example, when the reporter subunits, molecule of interest and the sub-cellular compartment localized molecule are proteins, they may be linked by methods known in the art for linkage peptides, e.g., expressed from a nucleic acid sequence as a fusion protein, as mentioned below in greater detail.

A given cell employed in the present method can be provided using any convenient protocol. For example, conjugates of the different molecules and reporter subunits can be introduced into a cell using a number of different protocols, e.g., microinjection, electroporation or a variety of bulk-loading techniques, or by providing in the cell nucleic acids that encode the different elements, e.g., in the form of fusion proteins.

In certain embodiments, the reporter subunit and the molecule of interest (or the sub-cellular compartment localized molecule) may make up a fusion protein that includes a reporter subunit and thus can be expressed from an encoding nucleic acid intracellularly. This system is advantageous in certain embodiments because it permits the detection and quantitation of sub-cellular compartment localization in cells, such as mammalian cells, based on enzymatic complementation of the reporter subunit. In certain embodiments, the molecule of interest and the sub-cellular compartment localization protein bind to one another, either directly or indirectly, when associated with the same sub-cellular compartment. In these embodiments, this interaction can increase the amount of complementation (and enzyme activity) by driving association between the reduced affinity reporter subunits. However, direct or indirect interaction between the molecule of interest and the sub-cellular compartment localization molecule when co-localized to the same sub-cellular compartment is not a necessary feature of the systems and methods of the present invention. Enzyme activity can be produced when the molecules of interest and the sub-cellular compartment localized molecule are in close proximity.

Fusion Proteins

Fusion proteins used herein include a single continuous linear polymer of amino acids which include the full or partial sequence of two or more distinct proteins, i.e., a protein of interest and a sub cellular compartment localized protein. Two or more amino acid sequences may be joined chemically, for instance, through the intermediacy of a cross-linking agent. In certain embodiments, a fusion gene construct includes a single continuous linear polymer of nucleotides which encodes the full or partial sequences of two or more distinct proteins in the same uninterrupted reading frame. Fusion gene constructs also may contain replication origins active in eukaryotic and/or prokaryotic cells and one or more selectables markers encoding, for example, drug resistance. They may also contain viral packaging signals as well as transcriptional and/or translational regulatory sequences and RNA processing signals.

In certain embodiments, the fusion gene constructs of the invention are introduced into cells to assay for sub-cellular compartment co-localization of the fusion protein encoded by the fusion gene constructs. The fusion gene constructs may also contain promoters and other transcriptional and/or translational regulatory sequences that are normally associated with the gene encoding the putative compound. The fusion gene construct may be introduced into cells by any method of nucleic acid transfer known in the art, including, but not limited to, viral vectors, transformation, co-precipitation, electroporation, neutral or cationic liposome-mediated transfer, microinjection or gene gun. Viral vectors of interest include, but not limited to: retroviruses, poxviruses, herpesviruses, adenoviruses, and adenoassociated viruses. In certain embodiments, retroviral vectors are employed, which are capable of stable integration into the genome of the host cell. For example, retroviral constructs encoding integration and packaging signals, drug resistance markers and one or more fusion genes of interest are useful in the practice of certain embodiments of the invention.

Different fusion gene constructs encoding unique fusion protein may be present on separate nucleic acid molecules or on the same nucleic acid molecule. In certain embodiments, the same vector is employed so that uptake of only a single species of nucleic acid by a cell is sufficient to introduce sequences encoding both putative binding partners into the cell. In terms of order of introduction, in those embodiments where the coding sequences are on different vectors, the vectors may be introduced into the cell simultaneously or sequentially. The present fusion gene construct or fusion proteins may be introduced into cultured cells, animal cells in vivo, animal cells ex vivo, or any other type of cell in which it is desired to study protein trafficking.

As will be understood by those skilled in the art, two fusion gene constructs are introduced into a single cell. The first is a fusion of a localization peptide and a EA β-galactosidase peptide. The localization peptide may be a FYVE domain peptide, a cell membrane localization peptide such as PH domain of phospholipase C gamma, etc. The second fusion gene construct comprises a target peptide sequence fused to an ED β-galactosidase peptide. This construct can be made by known genetic engineering methods using the nucleotide sequences given under the gene or protein database identifiers given here. The target peptide may be truncated or modified to have a misfolding mutation using known mutagenesis methods. The two genetic constructs will further comprise transcription sequences; plasmids known for such use are described in a number of the patents cited herein.

Test Compounds

The present methods provide means for assessing the ability of a test compound, or "compound" (small molecule, polypeptide, antibody, polynucleic acid etc.) to bind to a target peptide. The binding to the target peptide will cause the target peptide to be released from the first cellular compartment, and this release can be detected via EFC, where one enzyme fragment is fused to the target peptide. The example below describes a G-coupled receptor (GPCR) where a known mutation causes the receptor to be retained in the ER. The target peptide can be a protein with a known mutation that prevents it from leaving the ER until is bound by a test compound. The test compound may advantageously be a small molecule that can diffuse into the ER. The target peptide can be a mutated protein designed to be retained in the ER until bound by a test compound.

Evaluation of Reporter System Activity

Following provision of the cell comprising the molecule of interest and the sub-cellular compartment localized molecule each tagged (i.e., labeled) with a different subunit of the reporter system, the cell is then evaluated for activity of the reporter system, where the result of this evaluation step provides information about reporter system, where the result of this evaluation step provides information about fate of a target peptide in trafficking pathway.

In certain embodiments, evaluation includes detecting the activity and then comparing the observed activity to a reference or control value, e.g., a previously determined background activity value such as a level of $\beta$-galactosidase activity that is observed in a cell in which the reporter subunits are not co-localized to the same sub-cellular compartment (e.g., when the reporter subunits are fused to proteins that reside in distinct sub-cellular compartments), also called a background level. As developed in more details below, evaluation may include observing activity at two or more times during a given observation period, e.g., before and after contact of the cell with a test agent, etc., as may be required by a given assay protocol. This evaluation step may include providing a suitable substrate for the enzyme of the system, and detecting the enzyme mediated production of a detectable product there from, as described in more detail below.

Reporter System Assays

The reporter systems disclosed herein may be used to assay sub-cellular compartment co-localization of molecules attached to reporter subunits through complementation between the reporter subunits which produce a detectable signal. In one embodiment disclosed here, the co-localization of target peptide and sub-cellular localized protein can be detected and quantitated. The signal which is produced as the reporter subunits complement can serve as an indicator of the trafficking events. Exemplary signals include chromogenic, fluorescent and luminescent signals. These signals can be detected and quantitated visually or through the use of flow cytometers, spectrophotometers, fluorimeters, microscopes, scintillation counters or other instrumentation known in the art.

Association of components of the reporter systems disclosed herein will depend upon factors in solution, such as pH, ionic strength, concentration of components of the assay, and temperature. Assay solutions can be designed and developed for a particular system. The reporter systems disclosed herein can be used to conduct assays in solutions, such as buffered cell free solutions, cell interiors, solutions of cells, solutions of cell lysates and solutions of cell fractions, such as nuclear fractions, cytoplasmic fractions, mitochondrial fractions and membrane fractions. Methods for preparing assay solutions, such as enzyme assay solutions, cell extracts and cell suspensions, known in the art may be used. For example, physiologically compatible buffers such as phosphate buffered saline may be used. See for example, the series, Methods in Enzymology, Academic Press, New York.

In one embodiment, the reporter subunits are capable of complementing one another to form an enzymatically active complex that is capable of catalyzing the conversion of a substrate to a product which is detectable, either directly or indirectly. In one embodiment, the reporter system can include two or more components, each of which is a fusion protein, wherein the fusion proteins each comprise a protein (or polypeptide) fused to a low affinity reporter subunit. Thus, nucleic acids encoding the fusion proteins can be constructed, introduced into cells and expressed in cells. Alternatively, the presence of the complementing reporter subunits can be detected by detecting the binding of a labeled specific compound, such as an antibody, to the associated complementing reporter subunits.

In one embodiment, the low affinity reporter subunits may be complementing subunits of $\beta$-galactosidase, as reviewed in detail above. The system may include two, three or more reporter subunits, all of which are required to associate in order to produce the detectable signal. Methods for detecting the reaction products of active $\beta$-galactosidase that have been developed in the art may be used. For example, $\beta$-galactosidase activity may be measured by a range of methods including live-cell flow cytometry and histochemical staining with the chromogenic substrate 5-bromo-4-chloro-3-indolyl $\beta$-D-galactopyranoside (X-Gal). Nolan et al., Proc. Natl. Acad. Sci, USA, 85:2603-2607 (1988); and Lojda, Z., Enzyme Histochemistry: A laboratory Manual, Springer, Berlin, (1979). Histochemical staining for $\beta$-gal can be achieved by fixation of cells followed by exposure to X-gal.

Assays of $\beta$-gal activity as described in Mohler and Blau, Proc. Natl. Acad. Sci., 93: 12423-12427 (1996) may be used. In one embodiment, intracellular analyses may be conducted by fixing cells and staining with the indigogenic substrate X-gal. Fixed cells also can be analyzed by assaying for $\beta$-gal activity by fluorescence histochemistry using an azo dye in combination with either X-gal or 5-bromo-6-chloro-3-indolyl $\beta$-D-galactopyranoside (5-6-X-Gal). A combination of interest is the azo dye red violet LB (Sigma Chemicals, St. Louis, Mo.) and 5-6-X-Gal, referred to as Fluor-X-gal. For this combination, fluorescence micrographs can be obtained on a fluorescence dependent fluorescence to be visualized simultaneously with two or more other fluorescent signals.

Substrates of $\beta$-Galactosidase

Vital substrates for $\beta$-gal, which can be used in living cells, are also encompassed by the presently disclosed methods and materials. For example, a vital fluorogenic substrate, resorufin $\beta$-galactosidase bis-aminopropyl polyethylene glycol 1900 (RGPEG) has been described. Minden (1996) BioTechniques 20(1): 122-129. This compound can be delivered to cells by microinjection, electroporation or a variety of bulk-loading techniques. Once inside a cell, the substrate is unable to escape through the plasma membrane or by gap junctions. Another vital substrate that can be used in the practice of the presently disclosed methods and materials is fluorescein di-$\beta$-D-galactopyranoside (FDG), which is especially well-suited for analyses for analysis by fluorescence-activated cell sorting (FACS) and flow cytometry. Nolan et al., Proc. Natl. Acad. Sci, USA, 85:2603-2607 (1988) and Rotman et al. (1963) Proc. Natl. Acad. Sci, USA 50:1-6.

β-galactosidase may also be detected using a chemiluminescence assay. For example, cells containing β-galactosidase fusions are lysed (with or without contacting with a crosslinking agent) in a mixture of buffers containing Galacton Plus substrate from a Galactolight Plus assay kit (Tropix, Bedford Mass.) Bronstein et al, J Biolumin. Chemilumin., 4:99-111 (1989). After addition of Light Emission Accelerator solution, luminescence is measured in a luminometer or a scintillation counter.

Representative substrates that are suitable for spectrophotometric or fluoremetric analysis include, but are not limited to: p-aminophenyl-β-D-galactopyranoside; 4-methylumbelliferyl-β-D-galactopyranoside; mapthyl-AS-B1-β-D-galactopyranoside; 1-napthyl-β-D-galactopyranoside; 2-napthyl-β-D-galactopyranoside monohydrate; O-nitrophenyl-β-D-galactopyranoside; and phenyl-β-D-galactopyranoside, 5-bromo-4-chloro-3-indolyl-β-D-galactopyranoside, resorufin β-D-galactopyranoside, 7-hydroxy-4-trifluoromethyl coumarin, Ω-notrostyryl-β-D-galactopyranoside and fluorescein-β-D-galactopyranoside. See e.g., U.S. Pat. No. 5,444,161.

Additional Reporter Systems

Reporter systems other than β-galactosidase may also be used. For example, the enzyme β-glucuronidase (GUS) can be used as a reporter and chromogenic and fluorogenic GUS substrate have been developed. The GUS substrate 5-bromo-4-chloro-3-indolyl β-D-glucuronic acid (X-gluc) can be used in both chromogenic and fluoregenic applications, as follows.

The methods disclosed herein enable the monitoring of events taking place in the protein trafficking pathway in cell lysates, as well as in intact cells. Thus, interaction between fully folded proteins is detectable, and co-translational expression of the binding moieties is not necessary for binding to be detected.

The reaction product may be detected indirectly, for example, through immunological techniques, such as immunofluorescent labeling.

Utility

Embodiments of the invention can be used in a broad range of studies for monitoring proteins as they follow the trafficking pathway. In what follows, non-limiting examples of different applications of the methods of the invention are provided.

Membrane Trafficking

In certain embodiments, the subject methods are employed for studies involving membrane protein trafficking. Most of the cell surface receptors are regulated post-transcriptionally by the amount/number of receptors that will reach the cell surface to perform action. Thus, the activation and inhibition of the trafficking pathway can lead to dramatic cellular effects. E.g., the target peptide is fused to the first fragment of complementation assay and the second fragment is at a sub-cellular location which is located within the trafficking path of the target peptide. For instance, if the target peptide is localized to the ER then the second fragment could be localized to the endosome, lysosome, plasma membrane or Golgi complex. If the protein is induced to traffic further and progress towards its site of action then it would encounter the second enzyme fragment en route, i.e. in one of the cellular structures through which the protein passes, including the final compartment, typically the endosome. The increase in localization when the tagged target is in proximity to the labeled cellular structure will result in an increase in functional enzyme which then can be detected using a chemiluminescent or fluorescent substrate on live cells or in cell lysate.

The present assay and methods can also be carried out in the presence of extracellular signaling molecule, growth factors of differentiation factors, peptides, drugs or synthetic analogs or the like, whose presence or effects might alter the trafficking pathway of protein of interest in a particular cell type. E.g., GPCR's can be studies as discussed in more detail in the experimental section. Other factors that can affect protein trafficking can be the cell health, cell division or cell death and the like.

However, if the target peptide gets retained by the quality control mechanism of endoplasmic reticulum, the protein will not traffic further and thus no complementation will take place and hence no enzyme activity can be detected.

In certain embodiments, the presently disclosed methods and materials can be employed to assess the role of the binding moieties in the protein trafficking pathway. E.g., in this embodiment, the target peptide is a mutant/modified protein which is fused to the first fragment of complementation assay and the compound is fused to the second fragment of the complementation assay. As the target peptide is a mutant/modified protein, the quality control mechanism of endoplasmic reticulum will retain the protein and will not allow it to traffic further. Upon the addition of binding moieties, the quality control mechanism of endoplasmic reticulum will no longer recognize the target peptide as a misfolded protein and the target peptide will be able to exit the endoplasmic reticulum and follow the trafficking pathway and to reach the site of action.

In certain embodiments, the methods and compositions described here can be used to monitor modified GPCR's e.g., if the tail segment of GPCR is truncated/modified. In such instance, the modified GPCR is fused to the first fragment of complementation assay and the second fragment is fused with a sub-cellular localized protein in a sub-cellular organelle located within the trafficking path of the GPCR. As the modified GPCR moves within the trafficking pathway it will be retained in one of the sub-cellular organelle en route. If it encounters the second fusion protein a gain in signal will be observed. In this way we can monitor the changes that occur when GPCR's gets modified/mutated.

In another instance, the target peptide (which is a mutant/modified protein) is fused to the first fragment of complementation assay and the second fragment of complementation assay is at a sub-cellular location which is located within the trafficking path of the target peptide. Upon the addition of binding moieties the quality control mechanism of endoplasmic reticulum will no longer recognize it as a mis-folded protein. The protein will be allowed to exit endoplasmic reticulum and traffic further. The target peptide will then encounter the second fragment of complementation assay en route. The increase in localization will then result in a increase in functional enzyme which then can be detected using a chemiluminescent or fluorescent substrate on live cell or in cell lysates.

Heterodimerization and Trafficking

Dimerization, or higher order oligomerization of cell surface receptor is often a pre-requisite for receptor activation and ensuing signal transduction. The methods and compositions described here can also be used to study the heterodimerization process.

In certain embodiments binding partners of receptors can also be identified. E.g., certain receptors have been shown to only traffic to the cell surface in the presence of another/second protein. GABBR1 only expresses on the plasma membrane in the presence of GABBR2. In such instances, the target peptide will be fused to first fragment of complementation assay and is expressed in a cell background that expresses second fragment of complementation assay on plasma membrane/endosome. A third protein, as in this case is GABBR2 would then be introduced into the system. Each cell line resulting after the introduction of third protein would then be compared to the parental in terms of the amount of complemented enzyme. If GABBR2 was able to bind the target peptide (GABBR1) and enhance its plasma membrane/endosome localization, a gain of signal would be detected.

Additional Utilities

The studies can further be extended to taste receptors or olfactory receptors which are often difficult to study.

Additional utilities of the subject reduced affinity enzyme complementation reporter systems include but are not limited to those described in Published U.S. Patent Application Serial Nos. 20030219848; 20070275397; 20100285451; as well as in U.S. Pat. Nos. 4,378,428; 4,708,929; 5,037,735; 5,106,950; 5,362,625; 5,464,747; 5,604,091; 5,643,734 and PCT Application Nos. WO96/19732; WO98/06648; WO92/03559; WO01/0214; WO01/60840 and WO 00/039348; the disclosure of which are herein incorporated by reference.

Kits

Also provided by the subject invention are kits for use in practicing one or more of the above described applications. In certain embodiments, kits at least include a cell that expresses, either constitutively or inducibly, one or more fusion proteins that include a target peptide, a sub-cellular compartment localized protein, a compound and a reporter subunit, as reviewed above. In certain embodiments, kits include elements for making such cells, e.g., first and second nucleic acids encoding first and second fusion proteins present on the same or different vectors and/or nucleic acids encoding reporter subunits to which proteins of interest can be fused suing standard molecular biology techniques, as reviewed above. The kits may further include one or more additional components which find use in practicing certain embodiments of the invention, including but not limited to enzyme substrate, cell growth media, etc.

In certain embodiments, the present kits include (a) a cell comprising: (i) a first fusion protein comprising the target peptide and the first fragment of β-galactosidase (ii) the second fusion protein comprising the second fragment of β-galactosidase and a sub-cellular compartment localized protein; wherein the first and second fragments of β-galactosidase have an affinity for each other which is reduced as compared to the wild-type fragment; and (b) a β-galactosidase substrate. In certain embodiments, the one of the fragments of β-galactosidase is a variant minimal N-terminal β-galactosidase peptide. In one embodiment the localization of second fusion protein is on a sub-cellular compartment other than the sub-cellular compartment where the first fusion protein is retained. In one embodiment, the localization of second fusion protein and the first fusion protein are on the same sub-cellular compartment in a cell.

In certain embodiments, kits may include (a) a cell comprising: (i) a first fusion protein comprising the target peptide and the first fragment of β-galactosidase in the endoplasmic reticulum (ii) the second fusion protein comprising the second fragment of β-galactosidase and a sub-cellular compartment localized protein in a sub-cellular organelle other than ER; wherein the first and second fragments of β-galactosidase have an affinity for each other which is reduced as compared to the wild-type fragment (iii) compound; and (b) a β-galactosidase substrate. In certain embodiments, the one of the fragments of β-galactosidase is a variant minimal N-terminal β-galactosidase peptide. In one embodiment the localization of second fusion protein is on a sub-cellular compartment other than the sub-cellular compartment where the first fusion protein is retained. In one embodiment, the localization of second fusion protein and the first fusion protein are on the same sub-cellular compartment in a cell.

In certain embodiments, kits may include (a) a first nucleic acid encoding a first fusion protein comprises a target peptide and a first fragment of β-galactosidase; (b) a second nucleic acid encoding a second fusion protein that comprises a sub-cellular compartment localized protein and a second fragment of β-galactosidase; wherein the first and second fragments of β-galactosidase have an affinity for each other as compared to wild type β-galactosidase fragments. In certain embodiments the first β-galactosidase fragment is a variant minimal N-terminal β-galactosidase peptide and has a binding affinity for said second β-galactosidase fragment that is lower than a β-galactosidase fragment consisting of amino acids 3 to 92 of *E. coli* wild type β-galactosidase. In certain embodiments, the nucleic acid is present on a vector. In certain embodiments, the vector comprises a restriction site positioned on the vector such that when a protein coding sequences is inserted into the vector using the restriction site, the vector encodes a fusion protein of the protein and the β-galactosidase fragment. In certain embodiments, the kit further comprises a β-galactosidase substrate.

In addition to the above components, the subject kits may further include instructions for practicing the subject methods. These instructions may be present in the subject kit in a variety of forms, one or more of which may be present in the kit. One form in which these instructions may be present is as printed information on a suitable medium or substrate, e.g., a piece or pieces of paper on which the information is printed, in the packaging of the kit, in a package insert etc. Yet another means would be a computer readable medium, e.g., diskette, CD, etc., on which the information has been recorded. Yet another means that may be present is a website address which may be used via the internet to access the information at a removed site. Any convenient means may be present in the kits.

Exemplary GPCRs that may be studied using the present methods and that may be cloned into expression vectors in the present kits include the adrenergic receptor (e.g. ADRA1A, ADRA1B, ADRA1D, ADRA2A, ADRA2C, ADRB2), histamine receptor (e.g. HRH1, HRH2, HRH3, HRH4), serotonin receptor (e.g. HTR1A, HTR1B, HTR1D, HTR1F, HTR2A, HTR2B, HTR2C, HTR5A, HTR7B) dopamine receptor (DRD1, DRD2), muscarinic receptor (e.g. CHRM1, CHRM2) and angiotensin receptor (e.g. AGTR1).

In a model of retinitis, the rhodopsin GPCR was tagged with an ED, and its translocation was studied in response to addition of 9-cis retinol. A dose-response curve showed sensitive results via complementation. Also, AVPR2 (Arginine vasopressin receptor 2), a GPCR for which antagonists are used therapeutically, was studied with SR49059, a small molecule vasopressin V1a receptor antagonist. Again, dose response curve was obtained indicating that a viable assay could be developed using this target peptide. More than 200 mutations in the AVPR2 gene have been identified in people with nephrogenic diabetes insipidus. Most of these mutations cause the vasopressin V2 receptor protein to be misfolded into an incorrect 3-dimensional shape. Thus the present assay finds particular applicability in identifying compounds that bind to the AVPR2 gene product in the case of a misfolding mutation which occurs in humans.

The following additional examples are offered by way of illustrations and not by way of limitation.

EXAMPLES

Example 1

Reduced Affinity β-Galactosidase System

We recently described a low affinity enzyme complementation system for monitoring protein trafficking in a cell. Using β-galactosidase to achieve low affinity complementation, the classic α peptide first described by Jacob and Monod (1961) was truncated and mutated at specific residues based on the crystal structure in order to derive the α peptide (α*) that weakly complements the omega (ω) fragment. To assay inter-compartmental protein movement, one enzyme fragment, ω, was localized in particular region of the sub-cellular compartment and the small complementing α* peptide was fused to the protein of interest. The concentration of α* in the immediate vicinity of ω correlated with the amount of enzyme activity obtained in a dose-and-time dependent manner, serving as a genetically encoded biosensor for local protein concentration (T. S. Wehrman, C. L. Casipit, N. M. Gewertz, H. M. Blau, Nat Methods 2, 521 (July, 2005)). Due to their low affinity, the interaction of the α* and ωβ-galactosidase fragments is not sufficiently strong to maintain a complemented enzyme. As a result, the β-galactosidase activity obtained at any given time is a measure of the dynamic interaction of the two fragments, a reflection of their local concentration. This reduced affinity system is further described in U.S. application Ser. No. 11/132,764 filed on May 18, 2005, the disclosure of which system and its method of product as described in the experimental section of that application is herein incorporated by reference.

The system has been further employed to monitor the protein as it follows the trafficking pathway in a cell as a function of complementation of low affinity mutant sub-units of the β-galactosidase enzyme fused to the receptor proteins.

This combination of features is not found in other protein interaction detection systems based on energy transfer (Y. Xu, D. W. Piston, C. H. Johnson, Proc. Natl. Acad. Sci. USA 96, 151 (Jan. 5, 1999); B. A. Pollok, R. Heim, Trands Cell Biol 9, 57 (February, 1999)) or split enzymes including dihydrofolate reductase (J. N. Pelletier, F. X. Campbell-Valois, S. W. Michnick, Proc. Natl. Acad. Sci. USA 95, 12141 (Oct. 13, 1998)), β-lactamase (A. Galarneau, M. Primeau, L. E. Trudeau, S. W. Michnick, Nat Biotech 20, 619 (June, 2002); T. Wehrman, B. Kleaveland, J. H. Her, R. F. Baliant, H. M. Blau, Proc. Natl. Acad. Sci. USA 99, 3469 (Mar. 19, 2002)), luciferase (R. Paulmurugan, S. S. Gambhir, Anal Chem 75,1584 (Apr. 1, 2003)), and the previously described β-galactosidase (F. Rossi, C. A. Charlton, H. M. Blau, Proc Natl Acad Sci USA 94, 8405 (Aug. 5, 1997); F. Rossi, C. A. Charlton, H. M. Blau, Proc Natl Acad Sci USA 94, 8405 (Aug. 5, 1997)).

Example 2

Use of Reduced Affinity β-Galactosidase System to Monitor Trafficking of Mutant ADRB2, a G-Protein Coupled Receptor The ADRB2 is a G-protein coupled receptor containing seven transmembrane regions. It been shown that mutation of W158 to alanine can cause retention of the protein in the endoplasmic reticulum. Contacting the receptor with small molecules that bind to ADRB2 results in enhanced movement of the protein to the plasma membrane and endosomal compartments.

In this system we utilize two fusion proteins:

The first fusion protein used comprises the target peptide (ADRB2 W158A-PK) and the first fragment of complementation assay. This construct includes the W158 to alanine mutation. The second fusion protein used comprises endosome localized protein and the second fragment of complementation assay. Expression of both proteins inside a cell results in an amount of complementation that can be modulated by ADRB2 binding compounds.

In this experiment, cells expressing the ADRB2 W158A mutant fused to the first fragment of complementation assay (ProLink™ peptide) and the endosomal localized EA were treated with a variety of adrenergic agonists and antagonists, all known to bind to ADRB2. They are shown in Table 1 below:

TABLE 1

Treatment of ADRB2 W158A mutant cells fused to ProLink ™ and EA with adrenergic agonists and antagonists

| Well | Compound | Compound Class | [μM] | Trafficking 5-EA ADRB2 S/B | Arrestin W158A S/B | cAMP Gs ADRB2 S/B |
|---|---|---|---|---|---|---|
| C3 | Naftopidil 2HCl | antagonist | 10 | 6.8 | 1.0 | 1.0 |
| E6 | (S)-Timolol maleate | antagonist | 10 | 15.6 | 0.9 | 1.2 |
| E9 | Procaterol HCl | agonist | 10 | 78.2 | 21.3 | 15.2 |
| G6 | (−)-Cyanopindolol hemifumarate | antagonist | 10 | 17.1 | 1.0 | 1.8 |
| G10 | Propanolol HCl | antagonist | 10 | 12.0 | 0.9 | 1.3 |

Figure 4:
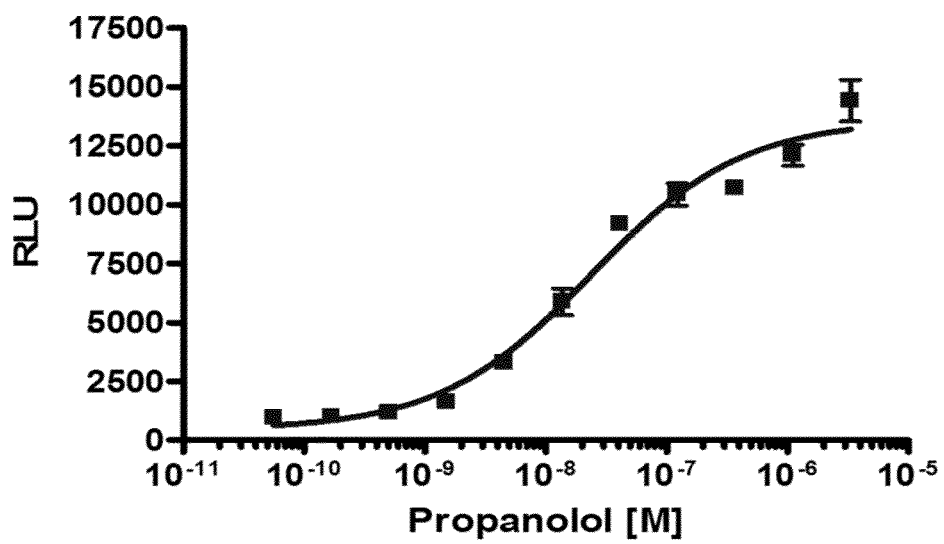
FIG. 4 is a graph of complementation occurring when a clonal cell line expressing ADRB2 (adrenergic, beta-2-, receptor, surface) (W158A)-PK is exposed to increasing concentrations of propanolol, an ADRB2 antagonist, overnight at 37° C. W158A, as is commonly understood, refers to a mutation at W 158 to A.

Results obtained with propanolol are plotted in a graph in FIG. 4. Analysis of those results is summarized in Table 2, shown below:

TABLE 2

Analysis of results from treatment of propanolol to cells expressing ADRB2W158A-PK Propanolol [M]

| Bottom | 430.4 |
|---|---|
| Top | 13600 |
| LOGEC50 | −7.625 |
| HILLSLOPE | 0.6928 |
| EC50 | 2.373e−008 |
| S/B = 14.9 | |

"Bottom" refers to the lowest concentration observed in the lower plateau.
"Top" refers to the highest concentration observed in the top plateau.
"LOGEC50" refers to the log of the $EC_{50}$ value.
"HILLSLOPE" refers to the steepness of the curve.
"EC50" refers to the half-maximal response of the compound.

The protocol used was as follows:
1) 5000 cells/well are plated in 20 μL assay media (MEME+10% FBS+1% Pen/Strep/Glut).
2) Cells are incubated overnight@37° C./5% $CO_2$.
3) 5 μL/well of a 5× dose response curve of compound is added to the cells.
4) Cells are incubated 16 hours@37° C./5% $CO_2$.
5) 12 μL/well PathHunter CL substrate is added to the wells.
6) Assay plate is incubated 1 hour@room temperature.
7) Assay plate is read on an Envision luminescence reader.
8) Data is plotted using GraphPad Prism, using the linear regression (variable slope) curve fitting function.

The cells were lysed and the complemented activity was measured using a chemiluminescent b-galactosidase substrate. The values of each well containing a test compound was divided by the signal obtained from the control wells that received only buffer. Evident from the table above is that the trafficking assay is able to detect the presence of agonist compounds and antagonist compounds, whereas the activity assays (Arrestin and cAMP) are only able to detect agonist compounds.

Example 3

Use of Reduced Affinity β-Galactosidase System to Monitor Trafficking of Mutant KCNH2 (hERG), Potassium Ion Channel The KCNH2 (hERG) is a gene that codes for a protein known as Kv11.1 potassium ion channel. Mutation in KCNH2 can result in the mis-folding of hERG protein and cause retention of the protein in ER whereas introduction of binding moieties results in the progress of protein through maturation path to the site of action.

In this system we utilize two fusion proteins:

The first fusion protein used comprises the target peptide (KCNH2-PK) and the first fragment of complementation assay. A single-point mutation is introduced in KCNH2. The second fusion protein used comprises plasma membrane localized protein and the second fragment of complementation assay. The second fragment of complementation assay was localized to the plasma membrane by fusing it to PH domain of phospholipase C gamma. Expression of both proteins inside a cell results in an amount of complementation that can be modulated by KCNH2 binding compounds.

In this experiment, cells expressing the KCNH2 mutant fused to the first fragment of complementation assay (Pro-Link™ peptide) and the plasma membrane localized EA were treated with a variety of compounds that bind to the ion channel.

Figure 5:
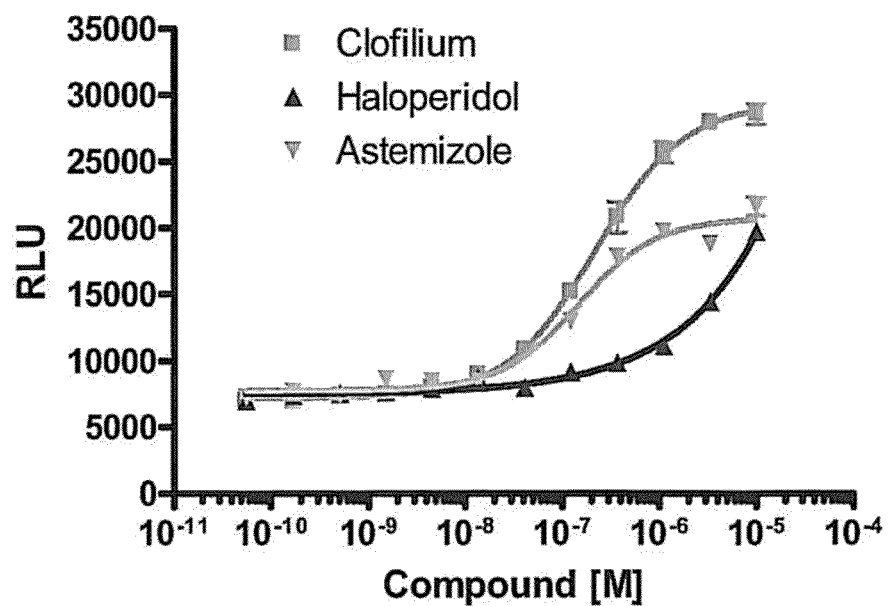
FIG. 5 is a graph of complementation occurring when a clonal cell line expressing KCNH2-(mutated)-PK is exposed to increasing concentrations of Clofilium (Herg channel blocker), Haloperidol, Astemizole, overnight.

Results obtained with variety of compounds (Clofilium, Haloperidol, Astemizole) are plotted in a graph in FIG. 5. Analysis of these results is shown in Table 3 below:

TABLE 3

Anlysis of results from treatment of compounds that bind to the ion channel KCNH2 mutant cells

|  | Clofilium | Haloperidol | Astemizole |
| --- | --- | --- | --- |
| BOTTOM | 7195 | 7500 | 7752 |
| TOP | 29361 | 537564 | 20737 |
| LOGEC50 | −6.657 | −1.815 | −6.826 |
| HILLSLOPE | 0.9507 | 0.5120 | 1.081 |
| EC50 | 2.205e−007 | 0.01531 | 1.494e−007 |

Another example of ion channel trafficking involves a single point mutation in KCNH2 which results in a misfolded hERG protein that is trapped in ER. Binding of ligand leads to stabilization ("rescue") and transport of the protein to the membrane. -PLC(PH)-EA anchors to the membrane. The assay did not work in Endo-EA cells, so it is probably unnecessary to express endo-EA for this assay. The assay is run overnight.

Example 4

Use of Reduced Affinity β-Galactosidase System to Monitor Trafficking of Mutant M4 (CHRM4), Acetylcholine Receptor The M4 (CHRM4) is muscarinic cholinergic receptors which belong to a larger family of G-protein coupled receptors. Deletion at the C-terminus can cause retention of the protein in ER. Addition of variety of small molecules that bind to CHRM4 results in enhanced movement of the protein to the plasma membrane and endosomal compartments.

In this system we utilize two fusion proteins:

The first fusion protein used comprises the target peptide (CHRM4 (DC)—PK) and the first fragment of βgalactosidase for use in the complementation assay. The CHRM4 (muscarinic cholinergic receptor 4) has an amino acid sequence as given at UniProt P08173. Links to appropriate DNA sequences are also found there. In this fusion, the CHRM4 has a deletion at the C-terminus that prevents trafficking of the fusion. Various mutations can be made that affect receptor folding and hence trafficking; see, e.g. Zheng et al. "Conserved Extracellular Cysteine Pair in the M3 Muscarinic Acetylcholine Receptor Is Essential for Proper Receptor Cell Surface Localization but Not for G Protein Coupling," J. Neurochem. 72:2404-2414 (1999).

The second fusion protein used comprises endosome localized protein/plasma membrane and the second fragment of β-galactosidase (EA). The second fragment of complementation assay was localized to the plasma membrane by fusing it to PH domain of phospholipase C gamma (See, Watt et al. "Subcellular localization of phosphatidylinositol 4,5-bisphosphate using the pleckstrin homology domain of phospholipase C deltal," Biochem J. 363:657-686 (2002). Expression of both proteins inside a cell results in an amount of complementation that can be modulated by CHRM4 binding compounds.

In this experiment, cells expressing the CHRM4 mutant fused to the first fragment of complementation assay (Pro-Link™ peptide) and the endosomal localized EA/plasma membrane localized EA were treated with a variety of compounds that bind to the ion channel.

Figure 6:
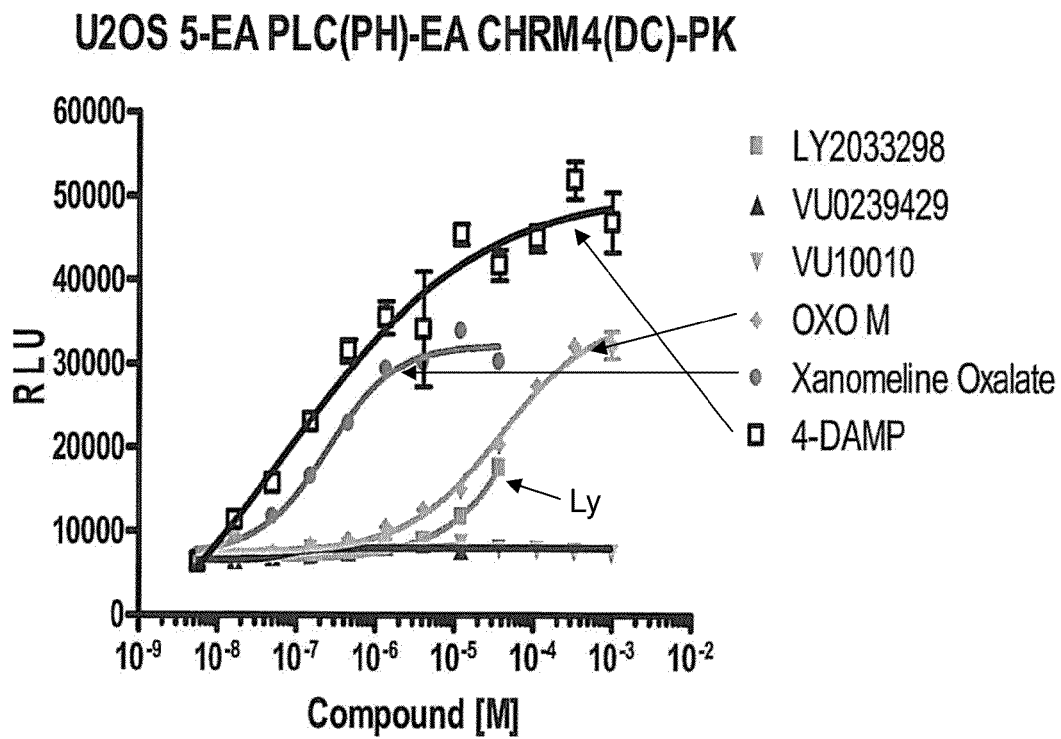
FIG. 6 is a graph of complementation occurring when a clonal cell line expressing CHRM4 (cholinergic receptor, muscarinic 4) (DC)—PK is exposed to increasing concentration of a number of ligands (LY2033298, VU0239429, VU10010, OXO M, Xanomeline Oxalate, 4-DAMP) overnight.

Results obtained with variety of compounds (LY2033298, VU0239429, VU10010, OXO M, Xanomeline Oxalate, 4-DAMP) are plotted in a graph in FIG. 6.

Conclusion

The above specific description is meant to exemplify and illustrate the invention and should not be seen as limiting the scope of the invention, which is defined by the literal and equivalent scope of the appended claims. All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not

What is claimed is:

1. A method of determining an effect of a compound on trafficking of a target peptide, comprising:
   a. providing a cell having an endoplasmic reticulum ("ER"), said cell comprising therein
      i. a first fusion protein comprising the target peptide fused to a first β-galactosidase fragment wherein the target peptide has a mutation causing retention of the first fusion protein in the ER; and
      ii. a second fusion protein comprising a protein localized to an endosome compartment fused to a second β-galactosidase fragment;
   b. wherein said first and second β-galactosidase fragments have an affinity for each other to complement and produce an active β-galactosidase enzyme only when the first and second β-galactosidase units are in close proximity;
   c. adding to said cell a compound that affects release of the target peptide from the ER; and
   d. evaluating said cell for active β-galactosidase activity to determine whether the first and second fusion protein interact in said sub-cellular compartment as a result of release of the target peptide from the ER being affected by the compound.

2. The method of claim 1 wherein said cell is a mammalian cell.

3. The method of claims 1 wherein said target peptide is a cell membrane protein.

4. The method of claim 3 wherein said cell membrane protein is a G-protein coupled receptor ("GPCR").

5. The method of claim 4 wherein the GPCR is one of a beta adrenergic receptor, histamine receptor, serotonin receptor, dopamine receptor, muscarinic receptor and angiotensin receptor.

6. The method of claim 1 wherein said first β-galactosidase fragment is an enzyme donor fragment.

7. The method of claim 1 wherein said second β-galactosidase fragment is localized to an endosome by a FYVE domain in said second fusion protein.

8. The method of claim 1 wherein the mutation is a single amino acid mutation.

* * * * *

UNITED STATES PATENT AND TRADEMARK OFFICE
CERTIFICATE OF CORRECTION

PATENT NO. : 8,569,057 B2  
APPLICATION NO. : 13/531230  
DATED : October 29, 2013  
INVENTOR(S) : Thomas S. Wehrman et al.

Page 1 of 1

It is certified that error appears in the above-identified patent and that said Letters Patent is hereby corrected as shown below:

IN THE CLAIMS:

Column 42, line 28 (Claim 3, line 1) delete "claims" and insert --claim--.

Signed and Sealed this
Twenty-ninth Day of March, 2016

Michelle K. Lee
*Director of the United States Patent and Trademark Office*